US006847336B1

(12) United States Patent
Lemelson et al.

(10) Patent No.: US 6,847,336 B1
(45) Date of Patent: *Jan. 25, 2005

(54) SELECTIVELY CONTROLLABLE HEADS-UP DISPLAY SYSTEM

(76) Inventors: Jerome H. Lemelson, Suite 286, Unit 802, 930 Tahoe Blvd. Incline Village, NV (US) 89451; John H. Hiett, 1060 W. Boulder La., Flagstaff, AZ (US) 86001

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/720,662

(22) Filed: Oct. 2, 1996

(51) Int. Cl.[7] .............................................. G09G 5/00
(52) U.S. Cl. ........................................................ 345/8
(58) Field of Search .......................... 345/7, 8, 9, 156, 345/157, 145, 146, 340, 348, 32; 351/210; 378/41, 42, 99

(56) References Cited

U.S. PATENT DOCUMENTS

| | | | |
|---|---|---|---|
| 3,724,932 A | 4/1973 | Cornsweet et al. ............ 351/7 |
| 3,923,370 A | 12/1975 | Mostrom ..................... 350/55 |
| 3,940,204 A | 2/1976 | Withrington ................ 350/3.5 |
| 4,028,725 A | 6/1977 | Lewis ....................... 358/103 |
| 4,181,405 A | 1/1980 | Cohen ....................... 350/331 |
| 4,188,050 A | 2/1980 | Ellis ......................... 350/174 |
| 4,349,815 A | 9/1982 | Spooner .................... 340/705 |
| 4,437,113 A | 3/1984 | Lee et al. ..................... 358/93 |
| 4,439,755 A | 3/1984 | LaRussa .................... 340/980 |
| 4,575,722 A | 3/1986 | Anderson ................... 340/783 |
| 4,613,219 A * | 9/1986 | Vogel ........................ 351/210 |
| 4,636,866 A | 1/1987 | Hattori ...................... 358/236 |
| 4,651,201 A | 3/1987 | Schoolman ................... 358/98 |
| 4,652,870 A | 3/1987 | Steward ..................... 340/705 |
| 4,669,810 A | 6/1987 | Wood ......................... 350/3.7 |
| 4,688,879 A | 8/1987 | Fairchild .................... 350/3.7 |
| 4,711,512 A | 12/1987 | Upatnieks ................... 350/3.7 |
| 4,725,125 A | 2/1988 | Ellis et al. ................... 350/174 |
| 4,729,634 A | 3/1988 | Raber ........................ 350/174 |
| 4,737,972 A | 4/1988 | Schoolman ................... 378/41 |
| 4,740,780 A | 4/1988 | Brown et al. ............... 340/705 |
| 4,763,990 A | 8/1988 | Wood ......................... 350/320 |
| 4,769,633 A | 9/1988 | Ellis .......................... 340/705 |
| 4,787,711 A | 11/1988 | Suzuki et al. ............... 350/174 |
| 4,796,987 A | 1/1989 | Linden ....................... 351/158 |
| 4,799,765 A | 1/1989 | Ferrer ........................ 350/174 |
| 4,818,048 A | 4/1989 | Moss ......................... 350/3.7 |
| 4,824,228 A | 4/1989 | Wickholm et al. .......... 350/516 |

(List continued on next page.)

OTHER PUBLICATIONS

Kancheral, A.R., et al., "A Novel Virtual Reality Tool for Teaching 3D Anatomy", Proc. CVR Med '95 (1995).

(List continued on next page.)

Primary Examiner—Chanh Nguyen
(74) Attorney, Agent, or Firm—Edwin A. Suominen; Douglas W. Rudy

(57) ABSTRACT

Systems and methods are disclosed for displaying data on a head's-up display screen. Multiple forms of data can be selectively displayed on a semi-transparent screen mounted in the user's normal field of view. The screen can either be mounted on the user's head, or mounted on a moveable implement and positioned in front of the user. A user interface is displayed on the screen including a moveable cursor and a menu of computer control icons. An eye-tracking system is mounted proximate the user and is employed to control movement of the cursor. By moving and focusing his or her eyes on a specific icon, the user controls the cursor to move to select the icon. When an icon is selected, a command computer is controlled to acquire and display data on the screen. The data is typically superimposed over the user's normal field of view.

14 Claims, 13 Drawing Sheets

U.S. PATENT DOCUMENTS

| | | | |
|---|---|---|---|
| 4,831,366 A | 5/1989 | Iino | 340/705 |
| 4,878,046 A | 10/1989 | Smith | 340/705 |
| 4,884,137 A | 11/1989 | Hanson et al. | 358/108 |
| 4,915,487 A | 4/1990 | Riddell, III et al. | 350/174 |
| 4,927,234 A | 5/1990 | Banbury et al. | 350/174 |
| 4,930,847 A | 6/1990 | Cederquist | 350/3.6 |
| 4,932,731 A | 6/1990 | Suzuki et al. | 350/3.7 |
| 4,961,625 A | 10/1990 | Wood et al. | 350/174 |
| 4,973,139 A | 11/1990 | Weinhrauch et al. | 350/345 |
| 4,984,179 A * | 1/1991 | Waldern | 345/848 |
| 4,987,410 A | 1/1991 | Berman et al. | 340/705 |
| 4,988,976 A | 1/1991 | Lu | 340/461 |
| 4,994,794 A | 2/1991 | Price et al. | 340/705 |
| 5,000,544 A | 3/1991 | Staveley | 350/174 |
| 5,003,300 A | 3/1991 | Wells | 340/705 |
| 5,005,009 A | 4/1991 | Roberts | 340/705 |
| 5,028,119 A | 7/1991 | Hegg et al. | 350/174 |
| 5,037,182 A | 8/1991 | Groves et al. | 359/630 |
| 5,066,525 A | 11/1991 | Nakamachi et al. | 428/29 |
| 5,108,479 A | 4/1992 | Hirano | 65/60.52 |
| 5,129,716 A | 7/1992 | Holakovszky et al. | 351/50 |
| 5,130,794 A | 7/1992 | Ritchey | 358/87 |
| 5,151,722 A | 9/1992 | Massof et al. | 351/158 |
| 5,162,828 A | 11/1992 | Furness et al. | 353/122 |
| 5,198,895 A | 3/1993 | Vick | 358/103 |
| 5,210,624 A | 5/1993 | Matsumoto et al. | 359/13 |
| 5,214,413 A | 5/1993 | Okabayashi et al. | 340/705 |
| 5,222,477 A | 6/1993 | Lia | 128/6 |
| 5,227,769 A | 7/1993 | Leksell et al. | 340/705 |
| 5,231,379 A | 7/1993 | Wood et al. | 340/705 |
| 5,231,674 A | 7/1993 | Cleveland et al. | 382/6 |
| 5,241,391 A | 8/1993 | Dodds | 358/209 |
| 5,243,448 A | 9/1993 | Banbury | 359/13 |
| 5,251,127 A | 10/1993 | Raab | 364/413.13 |
| 5,270,748 A | 12/1993 | Katz | 351/210 |
| 5,278,696 A | 1/1994 | Suvada | 359/629 |
| 5,281,957 A | 1/1994 | Schoolman | 345/8 |
| 5,281,960 A | 1/1994 | Dwyer, III | 345/31 |
| 5,287,437 A | 2/1994 | Deering | 395/127 |
| 5,302,964 A | 4/1994 | Lewins | 345/7 |
| 5,305,203 A | 4/1994 | Raab | 364/413.13 |
| 5,319,363 A * | 6/1994 | Welch et al. | 340/825.36 |
| 5,321,416 A | 6/1994 | Bassett et al. | 345/8 |
| 5,331,149 A | 7/1994 | Spitzer et al. | 250/221 |
| 5,331,333 A | 7/1994 | Tagawa et al. | 345/7 |
| 5,334,991 A | 8/1994 | Wells et al. | 345/8 |
| 5,341,181 A | 8/1994 | Godard | 351/210 |
| 5,341,242 A | 8/1994 | Gilboa et al. | 359/631 |
| 5,345,281 A | 9/1994 | Taboada et al. | 351/210 |
| 5,347,400 A | 9/1994 | Hunter | 359/815 |
| 5,348,477 A | 9/1994 | Welch et al. | 434/43 |
| 5,367,315 A | 11/1994 | Pan | 345/156 |
| 5,392,158 A | 2/1995 | Tosaki | 359/633 |
| 5,406,415 A | 4/1995 | Kelly | 359/633 |
| 5,414,544 A | 5/1995 | Aoyagi et al. | 359/53 |
| 5,416,876 A | 5/1995 | Ansley et al. | 385/116 |
| 5,421,589 A * | 6/1995 | Monroe | 345/9 |
| 5,430,505 A | 7/1995 | Katz | 351/208 |
| 5,436,765 A | 7/1995 | Togino | 359/631 |
| 5,436,841 A | 7/1995 | Ferro | 364/459 |
| 5,450,596 A | 9/1995 | Felsenstein | 395/800 |
| 5,452,416 A | 9/1995 | Hilton et al. | 395/161 |
| D363,279 S | 10/1995 | Ishizawa et al. | D14/124 |
| 5,457,356 A | 10/1995 | Parodos | 313/505 |
| 5,471,542 A | 11/1995 | Ragland | 382/128 |
| 5,473,365 A | 12/1995 | Okamura | 348/53 |
| 5,479,224 A | 12/1995 | Yasugaki et al. | 353/101 |
| 5,483,307 A | 1/1996 | Anderson | 353/98 |
| 5,485,172 A | 1/1996 | Sawachika et al. | 345/8 |
| 5,493,595 A * | 2/1996 | Schoolman | 378/41 |
| 5,526,812 A * | 6/1996 | Dumoulin et al. | 345/7 |
| 5,649,061 A * | 7/1997 | Smyth | 706/16 |
| 5,671,158 A * | 9/1997 | Fournier et al. | 345/8 |
| 5,712,649 A * | 1/1998 | Tosaki | 345/7 |

OTHER PUBLICATIONS

Fuchs, et al., "*Virtual Space Teleconferencing using a Sea of Cameras*", Proceedings of the First International Symposium on Medical Robotics and Computer Assisted Surgery, Pittsburgh, P.A., (Sep. 22–24, 1994).

Yoshida, et al., "*Optical Design and Analysis of a Head–Mounted Display with a High–Resolution Insert*", Proc. SPIE 2537, (1995).

Eddings, J. *How Virtual Reality Works*, Ziff–Davis Press, Emeryville, California, (1994).

Gagliardi, R., et al., *Optical Communications*, John Wiley & Sons, Inc., New York, (1995).

Lynch, C., et al., *Packet Radio Networks: Architextures, Protocols, Technologies and Applications*, Pergamon Press, New York, (1987).

Cabral, J., et al., "*Multimedia Systems for Telemedicine and Their Communications Requirements*", IEEE Communications Magazine, (Jul. 1996).

Tsiknakis, M., et al., "*Intelligent Image Management in a Distributed PACS and Telemedicine Environment*", IEEE Communications Magazine, (Jul. 1996).

Hutchison, A., "*Electronic Data Interchange for Health Care*", IEEE Communications Magazine, (Jul. 1996).

Schmandt, C., *Voice Communications With Computers*, Van Nostrand Reinhold, New York, (1994).

Baber, C., et al, *Interactive Speech Technology: Human Factors Issues in the Application of Speech Input/Output to Computers*, Taylor and Francis, PA, (1993).

Sullivan, J., et al., *Intelligent User Interfaces*, Addison–Wesley Publishing Company, New York, (1991).

Yoshida, A., et al., "*Design and Applications of a High Resolution Insert Head–Mounted–Display*", Proc. VRAIS' 95, pp. 84–93, (1995).

Williams, E., *Liquid Crystals for Electronic Devices*, Noyes Data Corporation, New Jersey, (1975).

Tidwell, M., et al., "*The Virtual Retinal Display—A Retinal Scanning Imaging System*", Proceedings of Virtual Reality World '95, pp. 325–334, Munich, Germany:IDG Conference and Seminars, (1995).

Kollin, J., "*Optical Engineering Challenges of the Virtual Retinal Display*", Proceedings of the SPIE, vol. 2537, pp. 48–60, Bellingham, WA, (1995).

Kollin, J. "*A Retinal Display for Virtual–Environment Applications*" Proceedings of Society for Information Display, 1993 International Symposium, Digest of Technical papers, vol. XXIV, p. 827, Playa Del Rey, CA: Society for Information Display, (1993).

Robinson, G., "*Display Prototype Uses Eye's Retina as Screen*", Electronic Engineering Times, pp. 33–34 (Apr. 1, 1996).

* cited by examiner

HMD USAGE EXAMPLE

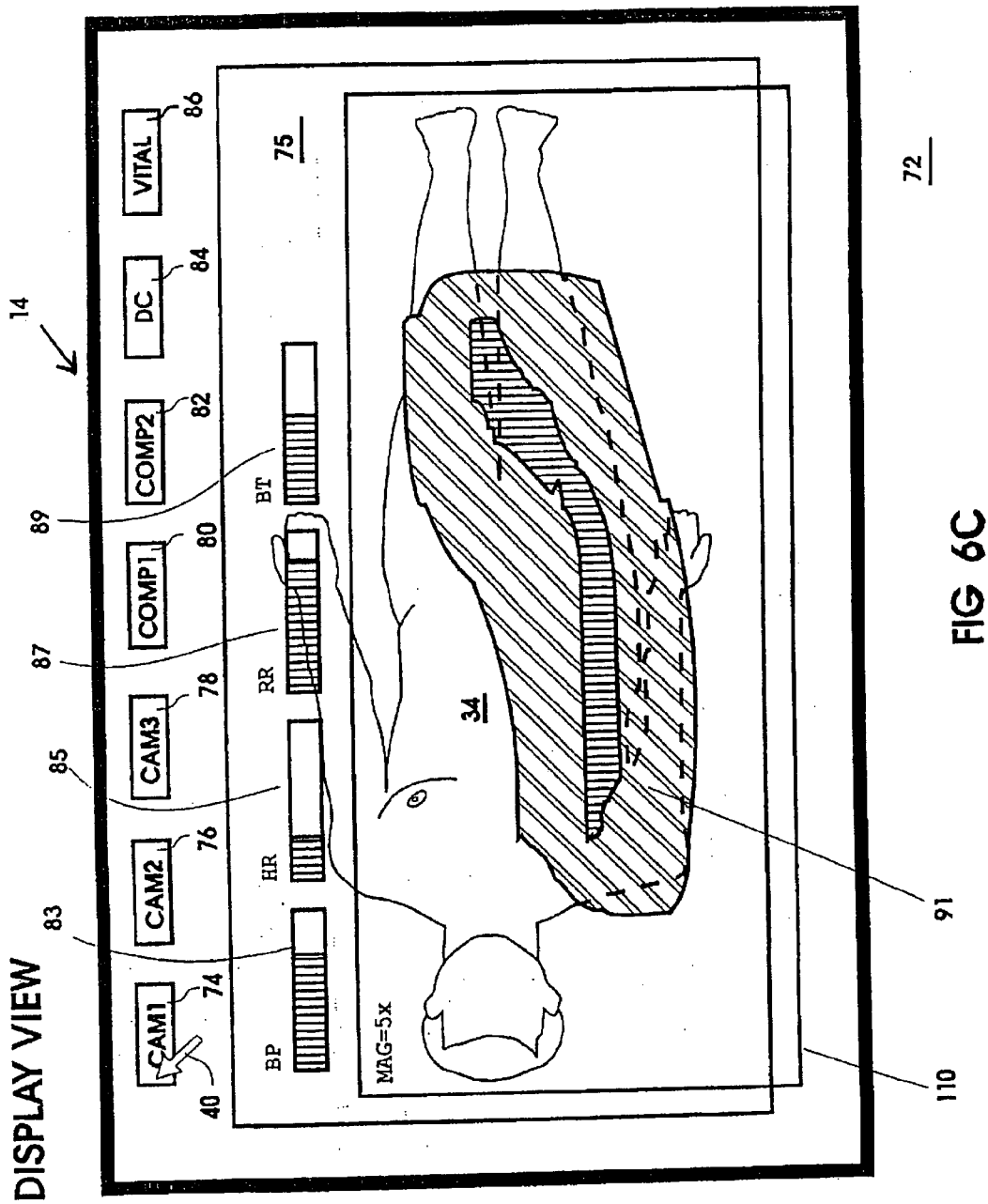

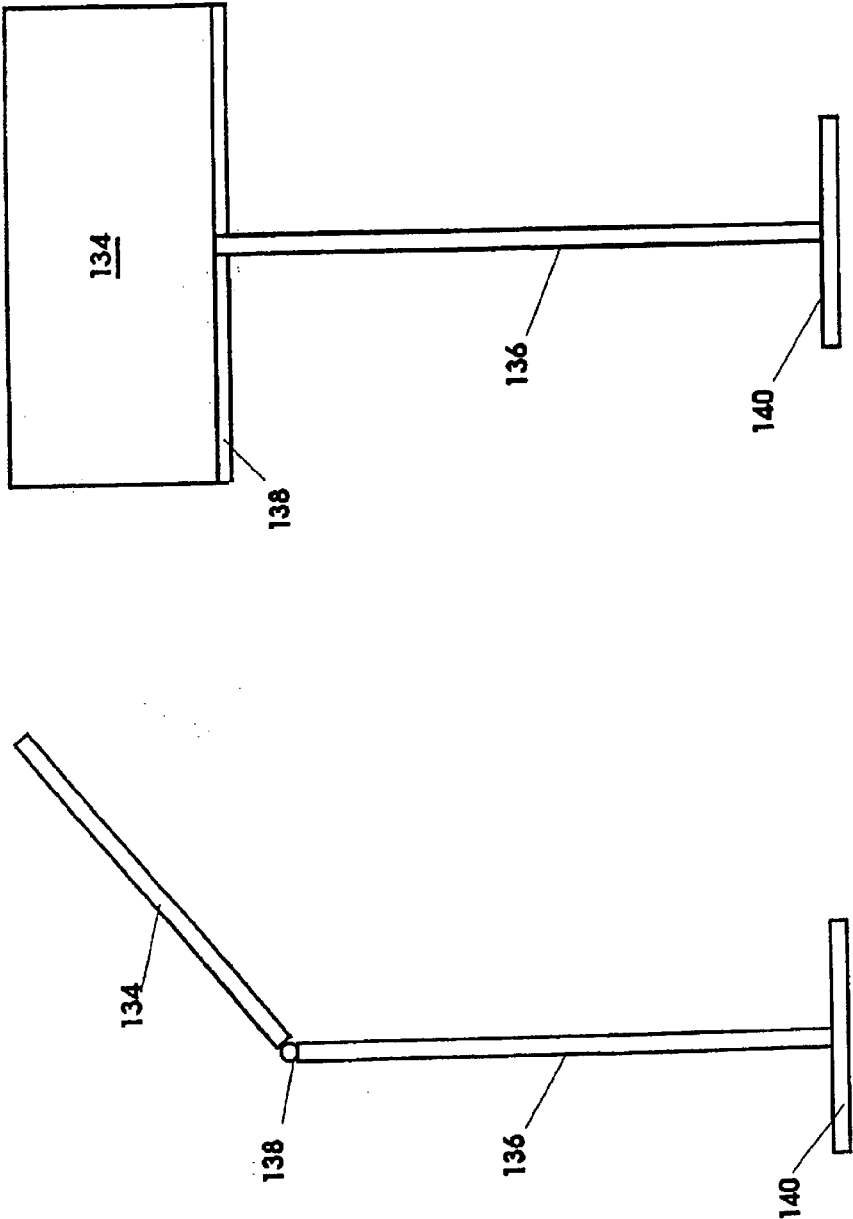

SELECTIVELY CONTROLLABLE HEADS-UP DISPLAY SYSTEM

FIELD OF THE INVENTION

The inventions relate to electronic display systems and control systems therefor. More particularly the inventions relate to selectively operable heads-up display systems for presenting information and/or image(s) to the user. In its preferred form, the heads-up display is configured for use by medical technicians or personnel, such as surgeons performing an operation.

BACKGROUND OF THE INVENTION

A heads-up display is generally defined as an electronically generated display containing information or data that is superimposed on an observer's normal field of view. As explained in greater detail below, heads-up display ("HUD") systems have been used in various applications. One such application is for use by pilots of aircraft. In the typical aircraft HUD system, a semi-transparent display screen is located generally in front of the eyes of the pilot (i.e. a screen mounted on the pilot's head or helmet, or in the view of the aircraft windshield). Such a system enables a pilot to concentrate on the difficult tasks associated with flying the aircraft, without diverting his attention to scan or examine a wide array of instruments.

It is also well known that medical technicians or personnel, such as surgeons, must keep track of many different types of information during an operation. For example, a surgeon must carefully view or monitor the physical surgery while simultaneously monitoring a patient's condition (e.g., blood pressure, heart rate, pulse, etc.). In addition, depending on the procedure, the surgeon must also monitor the status and settings of surgical equipment and tools. Although the additional information is necessary and important, monitoring such information often diverts the surgeon from the immediate task at hand.

Some surgical operations require that the surgeon divert his eyes to view a video monitor, for example, when performing highly complex laser or internal surgery conducted through scopes. See U.S. Pat. No. 5,222,477, which discloses an endoscope or borescope stereo viewing system. In addition, the surgeon may from time to time need to refer to data, such as defined by a patient's recorded or written history, or to previously taken x-rays or other computer generated images (e.g., CAT, NMR, 3D, etc.). For example, U.S. Pat. No. 5,452,416 discloses an automated system and a method for organizing, presenting, and manipulating medical images for viewing by physicians. See also U.S. Pat. Nos. 5,251,127 and 5,305,203, which disclose a computer-aided surgery apparatus that positions surgical tools during surgery or examinations. In each of the above-described systems, in order to view the displayed information, the surgeon must divert his or her eyes to a remote monitor.

Thus, surgeons use many different types of displays and must continually monitor many different sources of information. However, as more tools and sources of data become available to surgeons for use during operations, more opportunities for distraction arise. It is difficult for a surgeon to focus on his or her conduct during a surgical procedure while also continually shifting focus away from the patient to other monitors or indicators. Therefore, a need exists for conveniently, efficiently and accurately displaying to a surgeon various types and sources of information, views, and images of a patient undergoing a critical medical procedure.

As explained in greater detail below, prior attempts in the medical field to fulfill that need have been unsatisfactory.

For example, video signal sources have been adapted to scan views or images for different types of medical uses and applications. U.S. Pat. No. 4,737,972 to Schoolman ("Schoolman I") discloses a head-mounted device that provides stereoscopic x-ray images. Furthermore, U.S. Pat. No. 4,651,201 to Schoolman ("Schoolman II") discloses an endoscope that provides stereoscopic images of the patient on a display. Both Schoolman I and Schoolman II allows for the selective transmission of other video data to the display. However, Schoolman I and Schoolman II do not use a "see through" display that allows the surgeon to monitor both the environment around him and the video image. If the surgeon wishes to monitor or view the real-world environment, as opposed to the displayed graphics, the head-mounted display must be removed.

Efforts have also been made to use head-mounted displays in augmented reality simulations for medical applications wherein a desired image or three-dimensional model is superimposed on the real scene of a patient. For example, it was reported that a research effort in the Department of Computer Science at the University of North Carolina has attempted to develop a see-through head-mounted display that superimposed a computer-generated three-dimensional image of the internal features of a subject over the real-life view of the subject. Information describing those research efforts may be found on the World Wide Web in a document maintained by Jannick Rolland at the site on the World Wide Web Pages of the NSF/ARPA Science and Technology Center for Computer Graphics and Scientific Visualization at the University of North Carolina, Chapel Hill (http://www.cs.unc.edu/~rolland, cited February, 1996, copies of which are included in the information disclosure statement that has been filed concurrently with this application). That World Wide Web site in turn referenced the following publication: A. R. Kancheral, et al., "A Novel Virtual Reality Tool for Teaching 3D Anatomy," *Proc. CVR Med '95* (1995). Other research efforts at the University of North Carolina attempted to use a video see-through head-mounted display and a high-performance computer graphics engine to superimpose ultrasound images over the real view of the subject, thereby allowing a user to "see within" the subject. A set of trackers captured the motion of the body part with respect to the field of view of the user, and a computer updated the position of the body part in real time. The computer attempted to correlate the "tracked" position of the body with the three-dimensional model and to display the model on the heads-up display in a manner that gave the appearance of "x-ray vision."

In the above-described University of North Carolina research efforts, the focus was primarily to help teach students by superimposing a single computer-generated image over a moving, real-life, image of a subject. However, as explained in the associated literature, the "tracking" requirements made the research effort quite complicated, and the results appeared less than satisfactory. Moreover, such a teaching system is not applicable to the real-world environment of a surgeon, where the patient is not moved (and "tracking" is unnecessary), and where the surgeon needs or desires other information to be made readily available for viewing.

Still another research program associated with the University of North Carolina is described in Fuchs, et al., "Virtual Space Teleconferencing using a Sea of Cameras," *Proceedings of the First International Symposium on Medical Robotics and Computer Assisted Surgery* (Pittsburgh, Pa., Sep. 22–24, 1994). That article describes research efforts that attempted to use a multitude of stationary cameras to acquire both photometric and depth data. The acquired data was purportedly used to construct a remote site in accordance with the head position and orientation of a local participant. According to the article, each participant wears a head-mounted display to look around a remote environment having surface geometries that are continuously sensed by a multitude of video cameras mounted along the walls and ceiling, from which cameras depth maps are extracted through cross-correlation stereo techniques. Views acquired from several cameras are then displayed on a head-mounted display with an integrated tracking system to provide images of the remote environment. The explained purpose of the effort was to duplicate, at a remote location, a three-dimensional virtual reality environment of a medical room. However, the article does not disclose the use of see-through displays providing a surgeon with the ability to select and display additional forms of data, or to superimpose data over a real-life view of the patient or surgical site.

Another type of head-mounted display is described in Yoshida, et al., "Optical Design and Analysis of a Head-Mounted Display with a High-Resolution Insert," *Proc. SPIE* 2537 (1995). That article describes yet another research program associated with the University of North Carolina in which a small area of a high-resolution image is inserted on a large field of a low resolution image displayed on a head-mounted screen. The system is described as using eye-tracking information to dynamically place the high resolution insert at the user's gaze point. The system purports to provide the user with both high-resolution imagery and a large field of view. In essence, using eye-tracking electronics, the "inserted image" corresponding to the user's gaze point is converted from low resolution to high-resolution. However, as above, the user can not select additional or alternative forms of data or different images to be superimposed over the primary image on the head-mounted display.

Thus, few head-mounted displays have been developed for the medical industry, and all those described above have had limited purpose and utility. On the other hand, and as discussed briefly above, a wide variety of head-mounted devices are commonly used in military applications. As mentioned, aircraft pilots, tank commanders, weapon operators and foot soldiers have all used head-mounted displays to display various forms of weapon or image information along with other data defining the real-world environment of the person wearing the display. For examples of such systems, see the following U.S. Pat. Nos. 4,028,725; 5,281,960; 5,000,544; 5,227,769; 4,994,794; 5,341,242; 4,878,046; 3,940,204; 3,923,370; 4,884,137; 4,915,487; and 4,575,722. Likewise, helmet or head-mounted displays have also been used for motorcycle riders. U.S. Pat. No. 4,988,976 discloses a motorcycle helmet that displays data or information such as speed, time, rpm's, fuel, oil, etc. on the transparent visor (i.e. vacuum fluorescent display) of the rider. Head-mounted displays that are worn in front of the user's eyes or worn as eye spectacles also exist. For example, see the following U.S. Pat. Nos. 5,129,716; 5,151,722; 5,003,300; 5,162,828; 5,331,333; 5,281,957; 5,334,991; 5,450,596 and 5,392,158.

The field of virtual reality also has driven advances in the use of various types of head-mounted displays. For example, see the following U.S. Pat. Nos. 4,636,866; 5,321,416; 5,347,400; 5,348,477; 5,406,415; 5,414,544; 5,416,876; 5,436,765; 5,479,224; 5,473,365; D363,279; 5,485,172; 5,483,307; 5,130,794. See also the publication *How Virtual Reality Works*, by J. Eddings (Ziff-Davis Press, Emeryville, Calif., 1994), and the site maintained by Rolland (referenced above) relating to telepresence systems and augmented reality.

Advances have also been made in the area of heads-up displays or screens that are not attached to or worn by the user. Most commonly, such systems are employed in automotive or military environments, to provide vehicle performance, weapon status, and other data for the driver or pilot. For examples of such systems, see the following U.S. Pat. Nos. 5,278,696; 4,652,870; 4,711,512; 4,729,634; 4,799,765; 4,927,234; 4,973,139; 4,988,976; 4,740,780; 4,787,711; 4,740,780; 4,831,366; 5,005,009; 5,037,182; 5,231,379; 4,824,228; 4,763,990; 4,669,810; 4,688,879; 4,818,048; 4,930,847; 4,932,731; 5,198,895; 5,210,624; 5,214,413; 5,302,964; 4,725,125; 4,188,090; 5,028,119 and 4,769,633.

Numerous advances have occurred in the specific forms of, and materials used in, heads-up display systems. See, for example, U.S. Pat. Nos. 4,987,410 and 4,961,625 (use of Liquid Crystal Displays (LCDs)); U.S. Pat. Nos. 5,108,479 and 5,066,525 (laminating glass plates or panels); and U.S. Pat. No. 5,457,356 (making a flat panel head-mounted display).

Also pertinent to this invention is the field of eye-tracking to control various computer or imaging functions. Various systems unrelated to the medical field have used eye-tracking for controlling a field of view. For example, see U.S. Pat. No. 4,028,725, which discloses an eye and head tracking system that controls a beam-splitter and retains the high-resolution part of the image in the field of view. The eye-tracking is carried out by infrared detection (i.e. see U.S. Pat. No. 3,724,932). See also U.S. Pat. Nos. 5,287,437; 4,439,755; 4,349,815; 4,437,113; 4,028,725 (referenced earlier) and the article "Optical Design and Analysis of a Head-Mounted Display with a High-Resolution Insert," referenced above, particularly at footnote 19, which refers to the Eye-tracking Systems Handbook, Applied Science Laboratories, Waltham, Mass. (1992).

Finally, video recording systems for recording scenery and heads up displays have been taught by the prior art. U.S. Pat. No. 5,241,391 to Dodds ("Dodds") discloses a video camera system that records scene conditions and heads-up displays.

Notwithstanding the large number of articles and patents issued in the area of heads-up or head-mounted displays, there has been no such display that is designed for the special needs of individuals performing detailed but critical tasks on relatively stationary subjects. Such a system would be extremely useful to personnel working in the fields of medicine, forensics, and micro-electronics.

Presently, there is a need for a selectively operable, head-mounted, see-through viewing display system for presenting desired information and/or images to a user, while at the same time allowing the user to view the real-world environment in which he or she operates. There is a further need to provide a convenient selectable viewing system that can be easily controlled by an eye-tracking cursor and speech recognition to control different images or displays on a video monitor or to control a field of view, while keeping the user's hands free to conduct precision operations.

SUMMARY OF THE INVENTION

Accordingly, it is an object of this invention to provide an improved heads-up display system.

It is an other object of the invention to provide a "hands-free" heads-up display system that is useful to individuals performing detailed procedures, such as those working in the fields of medicine, forensics, micro-electronics, biotech, etc.

It is another object of the invention to provide an improved head-mounted display that allows the user to view both the subject and selected data.

It is another object of the invention to provide an improved heads-up display that includes a user-friendly interface to a command control computer.

It is another object of this invention to provide an improved heads-up display that interfaces with a command control computer and includes an eye-tracking cursor to select menus to control computer performance and the display of data.

It is another object of this invention to provide an improved heads-up display that interfaces with a command control computer and includes a speech recognition circuit to control computer performance and display of data.

It is another object of the invention to provide an improved heads-up display that can be positioned between a surgeon and a patient in the surgeon's line of sight.

It is another object of the invention to provide an improved heads-up display that allows the user to view the subject while simultaneously monitoring the output from a number of different information sources, including imaging devices and remote or networked computer systems.

It is another object of the invention to provide an improved heads-up display that allows a medical technician to control medical imaging devices to obtain images of select parts of a patient and to display those images on the heads-up display.

It is another object of the invention to provide an improved heads-up display that allows a user to control a computer to acquire and display data defining a subject's history while simultaneously viewing the subject.

It is another object of the invention to provide an improved method for conducting surgery on a patient while simultaneously obtaining access to and conveniently displaying on a heads-up display a variety of types of data relating to the patient.

It is another object of the invention to provide an improved method of controlling a heads-up display by employing a "point-and-click" type user interface and cursor controlled by tracking movement of the eye.

It is another object of the invention to provide an improved method of controlling a heads-up display by employing speech recognition, both alone and in combination with an eye-tracking cursor.

It is another object of the invention to provide an improved heads-up display system that allows the user to control tools or instruments in a hands-free manner.

It is another object of the invention to provide an improved heads-up display system that allows a surgeon to control surgical tools or other instruments in a hands-free manner.

It is another object of the invention to provide an improved heads-up display maintained in an eyepiece of a scope or instrument and that is controlled with integral eye-tracking and speech recognition systems.

The above and other objects are achieved in an improved, selectively controllable system for presenting desired data on a head-mounted (or "heads-up") display. The system includes a command computer processor for receiving inputs that represent data and for controlling the display of desired data. The computer communicates with and controls the heads-up display system, which is configured to display the desired data in a manner that is aligned in the user's field of view. The heads-up display includes a user interface incorporating "hands-free" menu selection to allow the user to control the display of various types of data. In its preferred form, the hands-free menu selection is carried out using an eye-tracking cursor and a speech recognition computer to point to and select specific menus and operations.

The above and other objects are also achieved in an user-controllable heads-up system for presenting medical data to a physician. The system includes a command control computer for receiving inputs defining medical data and for controlling the display of that data on a head's-up display screen in the normal field of view of the physician. The heads-up display provides the physician with a "user interface" including menus and associated operations that can be selected with an eye-tracking cursor. The system also includes a microphone and speaker so that a physician can communicate with other personnel and computers both locally and remote from the site. The command computer includes a speech recognition processor to respond to spoken commands of the physician. The command computer also communicates with and receives a wide array of data from other computers networked therewith. The physician can select the specific data to be displayed on the screen. In addition, the physician can, with the eye-tracking cursor, control various medical imaging devices.

The above and other objects are also achieved in a method of selectively displaying multiple forms of data on a head-mounted display. In accordance with the method, a see-through computer display screen is mounted on a head piece that is worn by the user. A command computer controls a user interface so that command icons or menus are displayed in a super-imposed manner on the see-through, head-mounted display, thereby allowing the user to see both the normal field of view and the user interface. The user interface is provided with a "point-and-select" type of cursor. An eye-tracking system is integrated with the command control computer and the user interface to monitor the user's eye movement and to correspondingly control movement of the cursor. The user selects various computer operations from menus contained in the user interface by moving the eye-tracking cursor to selected menus or icons. By using the eye-tracking cursor to select various computer operations, the user can control the command computer to selectively display on the see-through HUD screen numerous items of data or images, while still seeing the normal field of view.

The preferred embodiments of the inventions are described below in the Figures and Detailed Description. Unless specifically noted, it is the intention of the inventors that the words and phrases in the specification and claims be given the ordinary and accustomed meaning to those of ordinary skill in the applicable art(s). If the inventors intend any other meaning, they will specifically state that they are applying a special meaning to a word or phrase.

Likewise, the use of the words "function" or "means" in the Detailed Description is not intended to indicate a desire to invoke the special provisions of 35 U.S.C. Section 112, ¶ 6 to define his invention. To the contrary, if the provisions of 35 U.S.C. Section 112, ¶6 are sought to be invoked to define the inventions, the claims will specifically state the phrases "means for" or "step for" and a function, without also reciting in such phrases any structure, material or act in support of the function. Even when the claims recite a "means for" or "step for" performing a function, if they also recite any structure, material or acts in support of that means of step, then the intention is not to invoke the provisions of 35 U.S.C. Section 112, ¶ 6. Moreover, even if the inventors invoke the provisions of 35 U.S.C. Section 112, ¶ 6 to define the inventions, it is the intention that the inventions not be limited only to the specific structure, material or acts that are described in his preferred embodiments. Rather, if the claims specifically invoke the provisions of 35 U.S.C. Section 112, ¶ 6, it is nonetheless the intention to cover and include any and all structures, materials or acts that perform the claimed function, along with any and all known or later developed equivalent structures, materials or acts for performing the claimed function.

As a primary example, the preferred embodiment of this invention is configured for use by a surgeon performing an operation on a patient. However, the invention is equally applicable to any environment in which the user is conducting precision or detailed procedures with his or her hands on a relatively stationary subject, and where the user would find it advantageous to see data superimposed over the normal field of view. The potential applications are too numerous to mention, but would include forensics, microelectronics, biotechnology, chemistry, etc. Thus, even though the preferred embodiment refers to use by a surgeon, and to the acquisition and display of medical data, its applicability is much broader, and the claims should be interpreted accordingly.

Further, the description of the preferred embodiments make reference to standard medical imaging devices that are used to generate images to be displayed on the heads-up display. The disclosure specifically references several examples of such devices, including video cameras, x-ray devices, CAT and NMR scanners, etc. However, numerous other medical imaging systems are well known to exist, and most likely, numerous improved imaging devices will be developed in the future. Thus, the present invention does not depend on the type of imaging device that is implemented. The inventions described herein are not to be limited to the specific scanning or imaging devices disclosed in the preferred embodiments, but rather, are intended to be used with any and all applicable medical imaging devices. Likewise, the preferred embodiments depicted in the drawings show a single generic imaging device mounted on a manipulator arm. Numerous other tool and manipulator configurations, and multiple imaging devices, can be substituted for the single device.

Further, the specification in some places refers to several computers or controllers that perform various control operations. The specific form of computer is not important to the invention. In its preferred form, applicant divides several of the computing, control and analysis operations into several cooperating computers or embedded systems. However, with appropriate programming well known to those of ordinary skill in the art, the inventions can be implemented using a single, high power computer. Thus, it is not the intention to limit the inventions to any particular form or any number of computers, or to any specific computer network arrangement.

Likewise, the detailed description below shows at least two embodiments for the display screen. The preferred embodiment discloses the display screen mounted on the head of the user. The second embodiment shows the display screen positioned between the user and the subject, in a manner that is not mounted upon or supported by the head of the user. Additional embodiments also exist, and need not be disclosed. For example, the first embodiment can be modified for use in the eye-piece of a scope of any form, such as used in micro-electronics, biotech, medicine, forensics, chemical research, etc.

Similarly, the specific arrangement of the icons and menus that appear on the HUD screen, and the associated operations performed by those icons and menu items, are a matter of choice for the specific application. Thus, the invention is not intended to be limited to the specific arrangement and contents of the icons and menus shown and described in the preferred embodiments. For example, the icons and menu items for a selectively controllable heads-up display used by a dentist would likely be different than the arrangement used for a micro-electronics engineer.

Further examples exist throughout the disclosure, and it is not the intention to exclude from the scope of the invention the use of structures, materials or acts that are not expressly identified in the specification, but nonetheless are capable of performing a recited function.

BRIEF DESCRIPTION OF THE FIGURES

The inventions of this application are better understood in conjunction with the following Figures and Detailed Description of their preferred embodiments. The various hardware and software elements used to carry out the inventions are illustrated in the attached drawings in the form of block diagrams and flow charts. For simplicity and brevity, the Figures and Detailed Description do not address in detail features that are well known in the prior art, such as the literature listed in the Background of the Invention, above. However, to assure an adequate disclosure, the specification hereby expressly incorporates by reference each and every patent and other publication referenced above in the Background of the Invention.

FIG. 6C depicts an embodiment for the display view and associated icons and menu items as seen by the surgeon wearing the heads-up display, with a view from one of the cameras selected for display on a transparent or see-through screen.

FIG. 7D depicts another form for the display view and associated icons and menu items as seen by the surgeon wearing the heads-up display, with multiple forms of data and images displayed in various windows on a portion of the screen.

FIGS. 8A, 8B and 8C depict various views of an alternative embodiment implemented with a transparent heads-up display that is not worn by the surgeon, but rather, is movably stationed over the patient.

DETAILED DESCRIPTION

Figure 1:
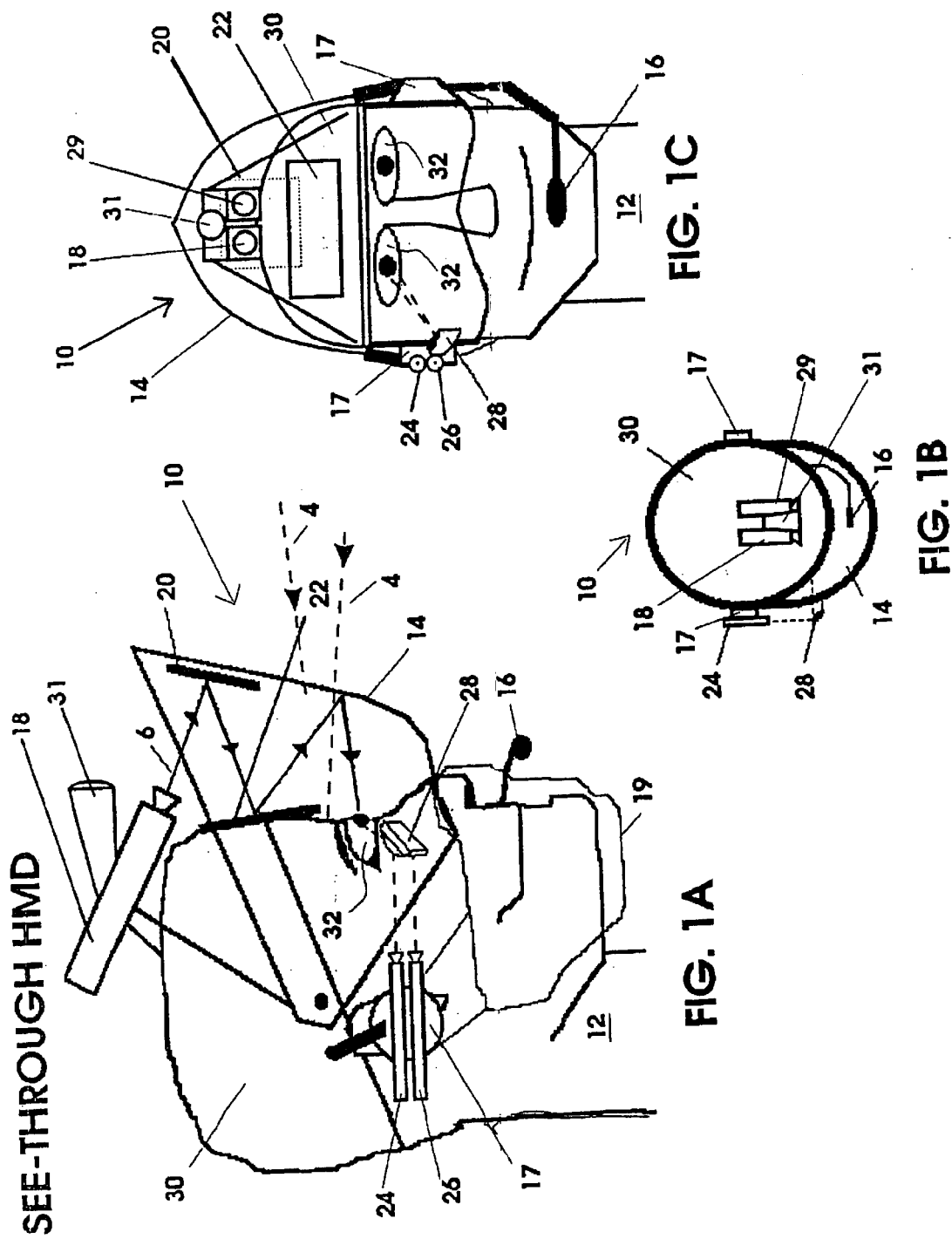
FIGS. 1A, 1B and 1C depict side, top and front views, respectively, of a selectable heads-up display worn by a technician, such as a surgeon.

Shown in FIGS. 1A, 1B and 1C are three views of a head-mounted, selectable, display system 10. In the preferred embodiment shown in the Figures, the display system 10 is worn by a surgeon 12 performing an operation. However, the system is easily programmed for use by any individual performing detailed procedures in which it is advantageous to see the normal field of view, while also having access to and seeing in that field of view a variety of forms of data relating to the procedure. Thus, it is envisioned that a display in accordance with this invention will have many applications, but is primarily intended for procedures where detailed work is performed on relatively stationary objects. Accordingly, while the description below refers repeatedly to the user as a "surgeon", it should be understood that the other users are included in the scope of the invention.

For convenience, the phrases "head-mounted display," "heads-up display" and "HUD" are used interchangeably throughout this specification. The major components of the HUD system 10 as worn by the surgeon 12 include a display screen 14, microphone 16, speaker 17, display driver 18, camera 29, display mirrors 20 and 22, light 31, eye-tracking laser 24, eye-tracking detector 26, and eye-tracking optics 28. In its preferred form, each of these components are integrated into a single, adjustable head piece that is placed on the surgeon's head 30. Once placed on a surgeon's head 30, the various components are adjusted for proper operation. More specifically, the screen 14 is positioned comfortably in front of and in the normal line of sight of the surgeon's eyes 32, and the microphone 16 (placed in front of surgical mask 19) and speaker 17 are positioned so that the surgeon 12 can communicate with selected medical assistants and computers including an electronic speech recognition system, as discussed in greater detail below. The display driver 18 and display mirrors 20 and 22 are adjusted to superimpose selected images and data with light rays 4 from outside of HUD 10 on the display screen 14 via optical path 6. Likewise, the eye-tracking laser 24, eye-tracking detector 26, and eye-tracking optics 28 are aligned to detect and communicate eye movement to an eye-tracking computer, as also discussed below. In more compact versions of the head mounted display system discussed above and shown in FIGS. 1A, 1B, 1C, and 2, an eyeglass frame may be used to support the display surface 14, eye-tracking laser 24, eye-tracking detector 26, eye-tracking optics 28, or other components as desired.

Figure 2:
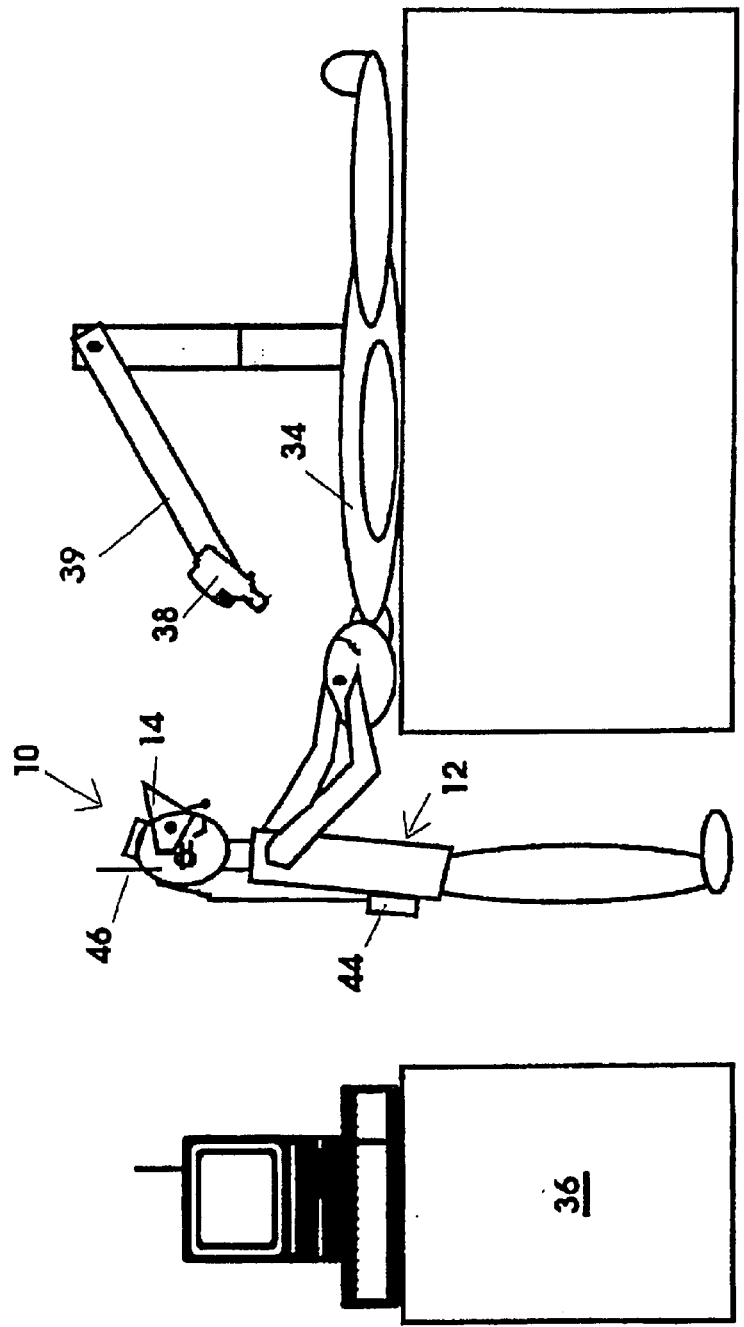
FIG. 2 shows an example for a basic configuration of an integrated head mounted display (HMD) and associated computer system used by a technician, such as a surgeon.

Referring to FIG. 2, the surgeon 12 wears the HUD system 10 to simultaneously view selected data and images while performing an operation on a patient 34. In a preferred form, the surgeon 12 can selectively control the display screen 14 to operate between opaque or translucent modes. In the opaque mode, the screen 14 will display primarily the data or images generated from a control computer 36 or one or more video or medical imaging input device(s) 38, for example, when conducting particularly detailed or internal surgery. In the translucent mode, the surgeon 12 will be able to see through display screen 14 to the patient 34, while at the same time seeing the data or images generated by the computer 36 or imaging input device(s) 38.

To simplify the disclosure, only one imaging input device 38 is shown in FIG. 2. However, it is expressly noted that multiple numbers, and any and all forms, of image-generating systems can be employed in the proposed system. Thus, CCD, video, x-ray, NMR, CAT, and all other medical imaging systems can be employed. In its most basic form, the imaging input device 38 is mounted on a moveable and computer controllable manipulator assembly or arm 39, so that it can be controlled by the surgeon 12 through the HUD system to move to selected parts of the patient 34, and to obtain and magnify images of particular parts of the body, tissue or organs undergoing surgery. For a more detailed discussion on automatically controlled and moveable cameras, see U.S. Pat. No. 5,249,045 and the patents cited therein, all of which are incorporated herein by reference.

In operation, the surgeon 12 can command the HUD system 10, under control of computer 36, to selectively display on screen 14 various forms of data, graphics or images, including magnified or otherwise modified images from the imaging input device(s) 38, while at the same time looking through the screen 14 to view the patient 34 and the normal, real-life environment of the operating room. Thus, the surgeon 12 is able to directly view the patient 34, while at the same time, select from many forms of data for display on the HUD screen 14. For example, if the surgeon 12 is performing surgery in close proximity to critical organs, the surgeon may wish to see both the movements of his or her hands, and a superimposed magnified view from one of the image input device(s) 38. The surgeon 12 can control the video device 38 to move to and focus on the critical area or surgical site, and to obtain and magnify and image for display on the HUD display 14. In addition, the surgeon can control the computer system 36 to record the generated images, and then to display on the HUD screen 14 selected parts thereof after being magnified or otherwise computer enhanced. In accordance with the invention, the surgeon 12 has the great advantage of being able to simultaneously control the HUD and data acquisition systems, while also looking through the HUD display 14 to watch minute hand movements and other aspects of the local environment.

As explained in greater detail below, the surgeon 12 may command the computer 36 in several ways. In the preferred mode, the HUD system 10 incorporates eye-tracking to control a cursor that is displayed on the HUD screen 14. More specifically, as shown graphically in FIGS. 6A–6C, the standard display 14 includes menu items or icons that can be selected by a cursor 40 that is in turn controlled by an eye-tracking system. For example, when the surgeon 12 focuses his eyes on a selected icon or menu displayed on the HUD screen 14, the eye-tracking system will correspondingly cause the cursor 40 to move or "track" over the selected icon or menu item. The surgeon can then select the specific icon or menu by voice command or with a foot-operated select button (not shown) operating in a manner similar to the well known "mouse" button. Thus, the surgeon operates eye-tracking cursor 40 in a "hands-free" manner to move onto icons and to select various imaging systems, computers or other data sources for display on the HUD display 14.

Alternatively, or in combination with the eye-tracking cursor 40, the HUD system 10 includes a standard speech recognition sub-system integrated with the command operations. Thus, the surgeon 12 can speak select speech commands or select words to select specific menus or to initiate computer operations to acquire and display select images or data. In the combined speech and eye-tracking mode, the surgeon can use his or her eye to move the cursor 40 to a particular menu or icon, and then speak commands to perform various operations associated specifically with that menu or icon, such as obtaining or magnifying images, selecting particular parts of patient histories, etc.

As shown in FIG. 2, the HUD display system 10 preferably communicates with the command computer 36 via any appropriate form of wireless communication, as is well known in the art of computer networking. Thus, the surgeon is shown wearing a radio transmitter 44 and an antenna 46 that operate in a manner that is well known in the art to communicate with computer 36. Although it is preferred to use wireless communication, it is expressly noted that any and all forms of wireless or wired communication can be used, and as a result, the invention is not intended to be limited to any specific form of data communication between the HUD system and the computer 36.

As discussed above, the surgeon may use the HUD system as a hands-free interface to control an imaging input device 38 (shown as a camera in FIG. 2) and its associated manipulator assembly 39 to obtain images of the patient 34, and to display the images on the HUD display 14. In addition, the surgeon can operate the HUD system as an interface to obtain from computer 36 (or from additional remote or local computers not shown) reference or other patient data, and to display that data on the HUD display 14.

Figure 3:
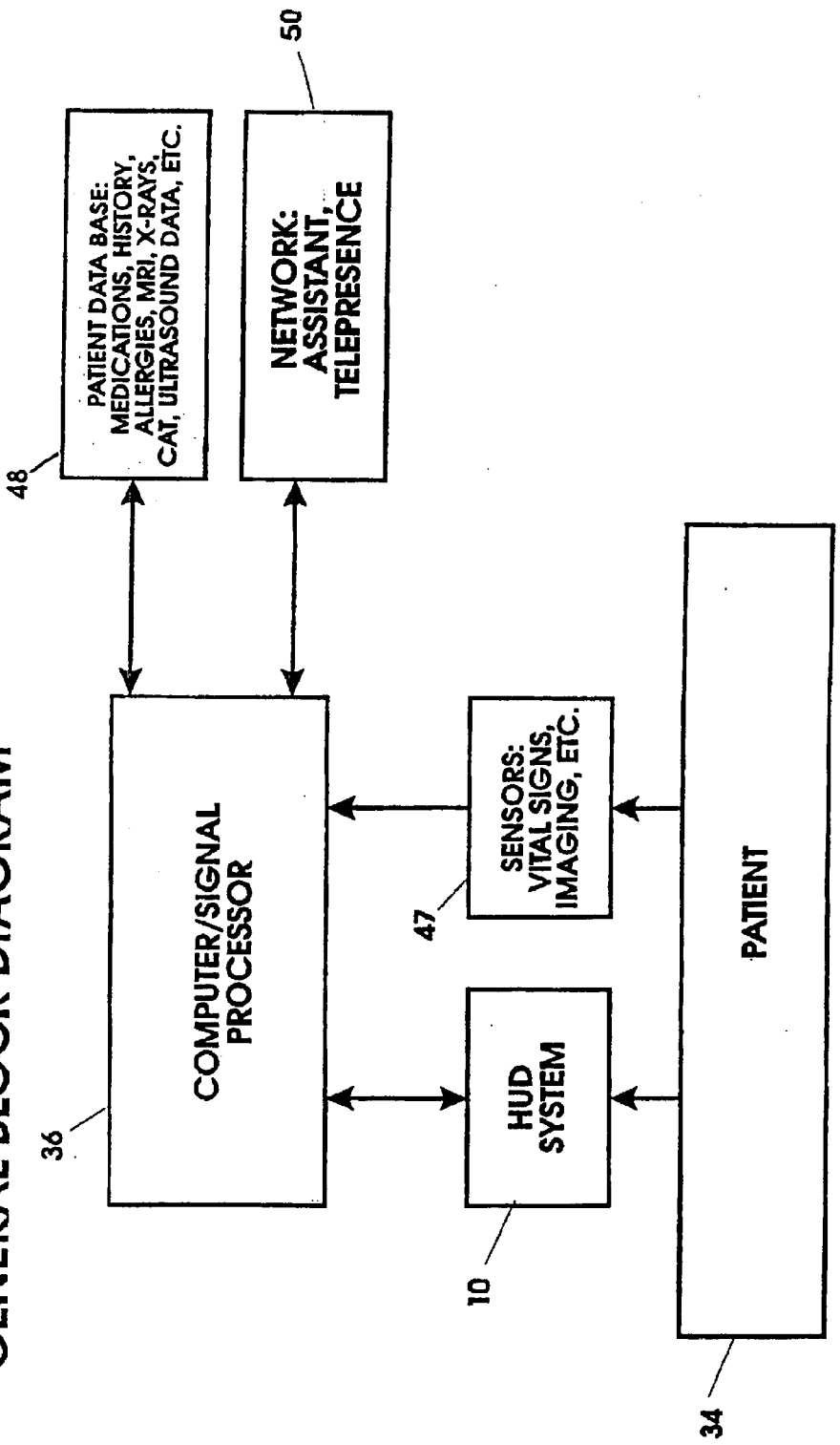
FIG. 3 is a block diagram of the primary components of the heads-up surgeon's display of FIG. 2.

Shown in FIG. 3 is a general block diagram of the HUD system integrated in a surgeon's environment in accordance with the present invention. The HUD system 10, including the referenced display, eye-tracking, speech recognition and communication elements, is coupled to a main command control computer 36. Also coupled to the command computer 36 are the numerous sensor inputs 47, such as those that monitor vital signs and acquire medical images. An electronic data base 48 of the patient's history is either coupled to or included in the memory of the command computer 36. The command computer 36 has access over a standard network 50 to remote sites and computers (not shown).

There are numerous types of sensor inputs 47 that will monitor the patient 34 and generate data of interest to the surgeon 12. Each such sensor 47 is considered old in the art, and operates to monitor and generate computer data defining the characteristics of the patient 34 in a manner well known to those of ordinary skill in the art. Thus, it is expressly noted that while several specific types of sensor inputs may be described in this specification, any and all types of sensor inputs 47 can be used, as long as the data is generated in a manner that is made accessible to the surgeon 12 by the command control computer 36.

The patient data base 48 includes any and all type of patient data that a surgeon may wish to access, including, for example, the patient's history and prior medical images. While the data base 48 is shown in FIG. 3 as being separate from the command computer 36, the data base can also be loaded into the data storage portion of the command computer 36. Likewise, the patient data base 48 may be located remote from the command computer 36, and can be accessed over the network 50.

In its preferred form, the network 50 may access not only the standard hospital network, but also remote sites. In that manner, the surgeon 12 can access and communicate with other computers, expert systems or data devices (not shown) that are both local and remote from the surgeon's location. Likewise, specialists remote from the specific operating site may view the operation and communicate or consult directly with the surgeon 12. More specifically, the remote sites can selectively display the operation from any number of cameras in the operating room, and in addition, can selectively display and view the procedure with the same perspective of the surgeon 12 through the HUD display screen 14, using the head-mounted camera 29. In that manner, specialists at the remote sites will see what the surgeon 12 sees, including the view of the patient 34 and the data, menus, icons and cursor shown on the HUD display screen 14. In its preferred form, the video camera 29 is a remote controlled, high-performance camera that is mounted on the HUD gear worn by the surgeon 12 so that it can selectively view and transmit an image of the HUD screen 14 to the command computer 36, and if desired, to a remote site or storage device (e.g., disk or video tape) controlled thereby. As shown in FIGS. 1B and 1C, the camera 29 can be mounted on the head of the surgeon 12 in a manner so as to make use of the same optics 20 and 22 used by the display driver 18. In addition, as described below, the head mounted camera 29 and/or imaging device 38 may be mounted instead to the robotic arm 39 controllable by the surgeon to tilt, pan, zoom or otherwise focus upon, selected views of the patient. The head mounted camera 29 may also be mounted other than on the top of the surgeon's head. For example, the camera 29 can be mounted on the left side of the surgeon's head, wherein additional optics are used to scan the display screen 14.

Figure 4:
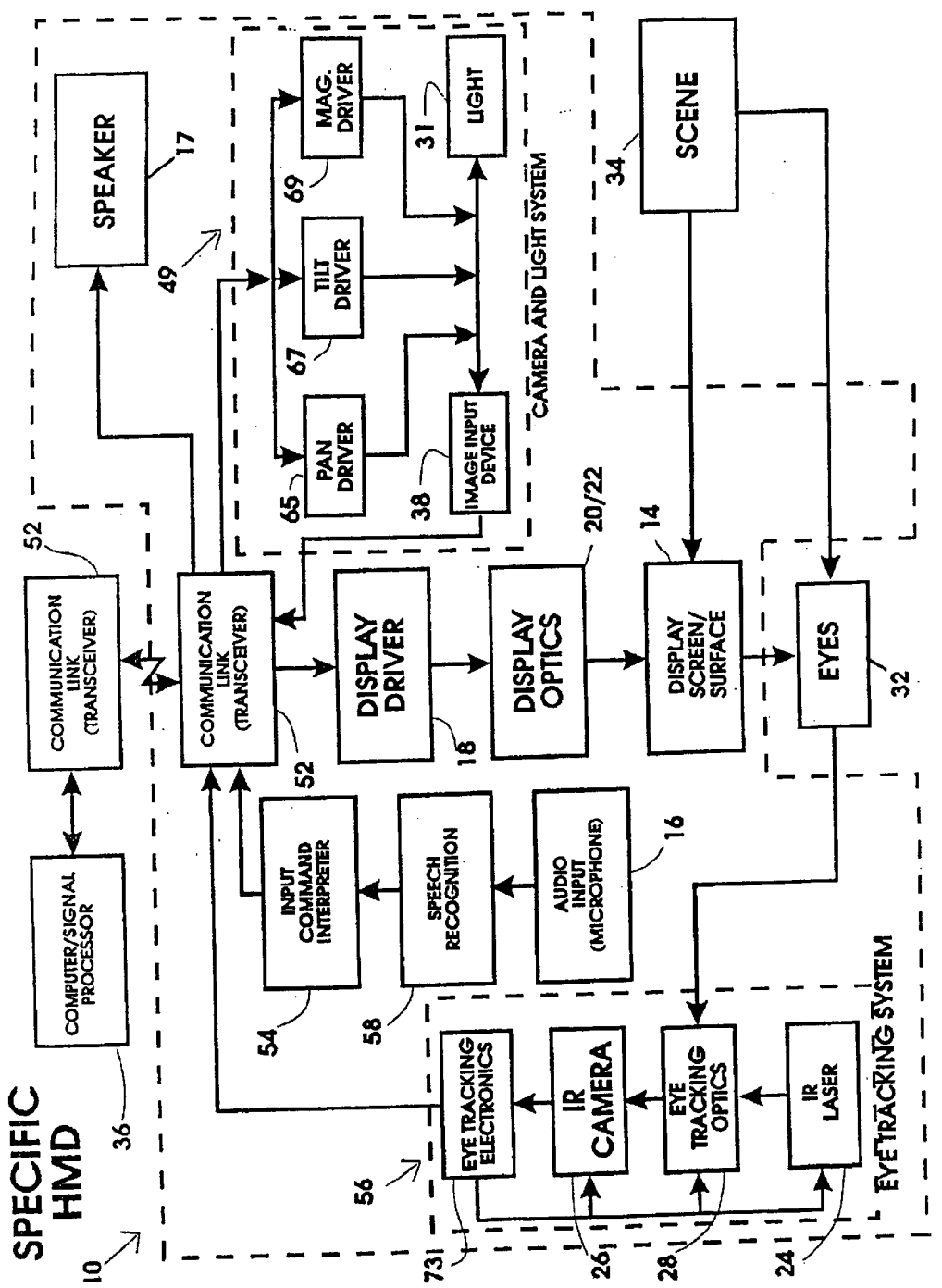
FIG. 4 is a more detailed block diagram of a preferred embodiment of the heads-up display system.

FIG. 4 shows a more specific diagram of the main components of the HUD display system 10. The HUD system 10 is coupled to and communicates with the command control computer 36 via a communication link 52. In its preferred form, the communications link comprises of two high speed digital radio transceivers or a optical communication system using fiber optic cable. The link allows for video, audio, and/or data to be transported to and from a computer network to and from the operator in the form of graphics, audio, video, text, or other data. For examples of such systems, see R. Gagliardi et al., *Optical Communications*, (John Wiley & Sons, Inc. NY, 1995), C. Lynch et al., *Packet Radio Networks: Architectures, Protocols, Technologies and Applications*, (Pergamon Press NY, 1987), J. Cabral et al., "Multimedia Systems for Telemedicine and Their Communications Requirements," *IEEE Communications Magazine* (July 1996), M. Tsiknakis et al., "Intelligent Image Management in a Distributed PACS and Telemedicine Environment," *IEEE Communications Magazine* (July 1996), and A. Hutchison, "Electronic Data Interchange for Health Care," *IEEE Communications Magazine* (July 1996). The above publications are incorporated herein by reference. It is noted that the communication link 52 can use any method of communicating appropriate signals or information to and from a computer system and/or network (i.e. including but not limited to a radio transceiver, fiber optic cable, wire etc.).

One use of the communication link 52 is to transmit to the command control computer 36 the input commands 54 generated by the surgeon 12. The surgeon 12 generates the input commands 54 in one or more of several alternative manners. Primarily, the commands 54 are generated when an eye-tracking system 56 detects the surgeon's eyes 32 focusing on selected icons or menu items displayed on the HUD screen 14. The icons and menu items then cause the initiation of a corresponding operation, as is common with standard icon-based user interfaces employed with computers running the Macintosh or Windows 95 operating systems. Alternatively, the surgeon 12 may generate the commands orally by speaking select words or commands through microphone 16. A standard voice recognition subsystem or computer 58 interprets the oral sounds output by the microphone 16, and generates digital commands 54 in accordance with well known speech recognition processes. These speech commands 54 are then passed to command control computer 36 through communication links 52. For more information on standard speech recognition systems, see C. Schmandt, *Voice Communication With Computers*, (Van Nostrand Reinhold, NY, 1994), and C. Baber et al., *Interactive Speech Technology: Human Factors Issues in the Application of Speech Input/Output to Computers*, (Taylor and Francis, PA, 1993), incorporated herein by reference. For more information on programming icon or menu based user interfaces, see J. Sullivan et al., *Intelligent User Interfaces*, (Addison-Wesley Publishing Company, NY, 1991), incorporated herein by reference.

The communication link 52 is also responsible for routing video images from a camera and lighting system 49 configured on the HUD system. More specifically, the camera and lighting system 49 generate video information under control of the surgeon 12 for display on the HUD screen 14. Thus, using commands generated by speech or from the icon/menu system, the surgeon controls pan driver 65, tilt driver 67, magnification driver 69 and light 31 to focus upon selected scenes for imaging. The pan driver 65 controls pivotal movement in the horizontal direction by the camera while the tilt driver 67 controls the vertical pivotal scanning movement of the camera. The magnifier driver 69 controls the degree of zoom of the image input device 38. The camera drivers each control a respective servomotor, stepper motor or actuator that moves or controls the associated camera parameter. In that manner, the surgeon can control the camera to focus upon and scan a particular feature (such as a tumor), and to generate and display on the HUD screen 14 highly magnified views thereof. In addition, the head mounted camera 29 can be controlled to scan the HUD screen 14 to generate, record and transmit to remote sites the view as seen by the surgeon 12. Although only one head mounted camera 29 is actually shown in the drawings, it should be understood that multiple cameras can be used, including multiple different types of cameras (such as video, television, infra-red), and that those and additional cameras may be controlled by other than the surgeon 12. Thus, the imaging input device 38 can either be controlled manually and/or automatically.

In addition to routing input commands 54, eye vector information from eye-tracking system 56, and data from image input device(s) 38 to the command control computer 36, the communication links 52 also serve to route control information from the command computer 36 to the HUD system 10 to operate the various subsystems such as the speaker 17, display driver 18, display screen 14, and imaging input device 38. More specifically, the command computer 36 operates to maintain the contents of the display on HUD screen 14, including maintaining the display of the basic menus and icons in accordance with the mode selected by the surgeon 12, controlling and displaying movement of the cursor 40 (shown in FIGS. 6A, 6B, and 6C) in response to the eye-tracking system 56 and/or speech recognition system 58, and displaying data and images obtained from the numerous available sources.

Thus, the command computer 36 regularly communicates, through communication links 52, the control signals necessary to operate the display driver or generating system 18, which in turn creates and projects the required elements of the basic user interface through the display optics 20/22 onto the HUD screen 14. As the surgeon 12 moves his eyes 32 to focus upon the various icons and menus of the user interface, the eye-tracking system 56 generates input signals for the command computer 36, which in turn controls the display generating system 18 to correspondingly move the cursor 40 (shown in FIGS. 6A, 6B, and 6C) on the display screen 14 in a manner that tracks the movement of the surgeon's eyes 32. At the same time, the command computer 36 updates the status and contents of the various menus and icons, in a manner familiar to those who use a "point-and-click" user interface, such as found in common Windows '95 and Macintosh computer systems using a mouse, touch-pad or similar device. As various menus and icons are selected, further input signals 54 are generated for use by the command computer 36, for example, to obtain patient data or past or current images. In response, the command control computer 36 carries out the required operations external to the HUD system 10 (such as controlling the sensor inputs 47 which may include imaging input device 38 or inputs from data base information 48 or other network 50 as shown in FIG. 3) to access and obtain the requested data. The command computer 36 then controls the HUD system 10 via communication links 52 to update the screen 14 to display for the surgeon the requested data or images, and to generate audio through speaker 17.

The display driver or generating system 18, shown in FIG. 4, operates to generate the images that are transmitted through the optics 20/22 and displayed on the HUD screen 14. Such display drivers or systems are well known to those of ordinary skill in the art, and any applicable display system can be used. For example, it is known to use display generating devices such as CRTs, LEDs, laser diodes, LCDs, etc., and this invention is not limited to any particular system, as long as it can generate and display video or computer-generated images onto the display surface/screen 14 or directly into the user's eyes 32 thereby superimposing images over the surgeon's actual field of view. See, for example, the following references related to display systems, each of which are incorporated herein by reference: A. Yoshida et al., "Design and Applications of a High-Resolution Insert Head-Mounted-Display", *Proc. VRAIS' 95* (pgs. 84–93, 1995), E. Williams, *Liquid Crystals for Electronic Devices* (Noyes Data Corporation, NJ, 1975); M. Tidwell et al., "The Virtual Retinal Display—A Retinal Scanning Imaging System," *Proceedings of Virtual Reality World '95* (pgs. 325–334, Munich, Germany: IDG Conferences and Seminars, 1995); J. Kollin, "Optical Engineering Challenges of the Virtual Retinal Display," *Proceedings of the SPIE* (Vol. 2537, pgs. 48–60, Bellingham, Wash., 1995); J. Kollin, "A Retinal Display for Virtual-Environment Applications," *Proceedings of Society for Information Display* (1993 International Symposium, Digest of Technical Papers, Vol. XXIV, pg. 827, Playa del Rey, Calif.: Society for Information Display, 1993) and G. Robinson, "Display Prototype Uses Eye's Retina as Screen," *Electronic Engineering Times* (pgs. 33–34, Apr. 1, 1996).

In its preferred form, the HUD system 10 uses a projection method for displaying images in the user's field of view using a light source (e.g. CRT, LED, laser diode, LCD projector, etc.). The light source intensity or brightness can be varied in the user's field of view so that the image being displayed can be more visible than the surrounding light. The light source intensity may also be decreased so that the surrounding light can become more visible and the image being displayed less visible.

Most CRT, LED, and other projection display methods require distance (optical path length) for projecting images. Thus, as shown in FIG. 1, a CRT/LED projector 18 is used as the display driver. In order to make the display screen 14 as small as possible, display mirrors 20 and 22 are used to transmit the projected images to the screen 14. More specifically, mirrors 20 and 22 are located within the head-mounted system 10, and are positioned outside of the field of view of the user 12. However, they reflect the projected image so that it can be superimposed over a real scene on the display screen/surface 14 formed of a glass or other suitable display material. Another method of displaying images in the user's field of view is by using LCD technology embedded inside the display surface 14. Here light from the surrounding environment is blocked or filtered by the display when the appropriate voltage is applied to cells in a LCD matrix. Part of the control of the display screen 14 is done through eye-tracking system 56. This eye-tracking system 56 includes eye-tracking electronics 73, an infrared camera 26, eye-tracking optics 28, and an infrared laser 24, all of which are described below.

Figure 5:
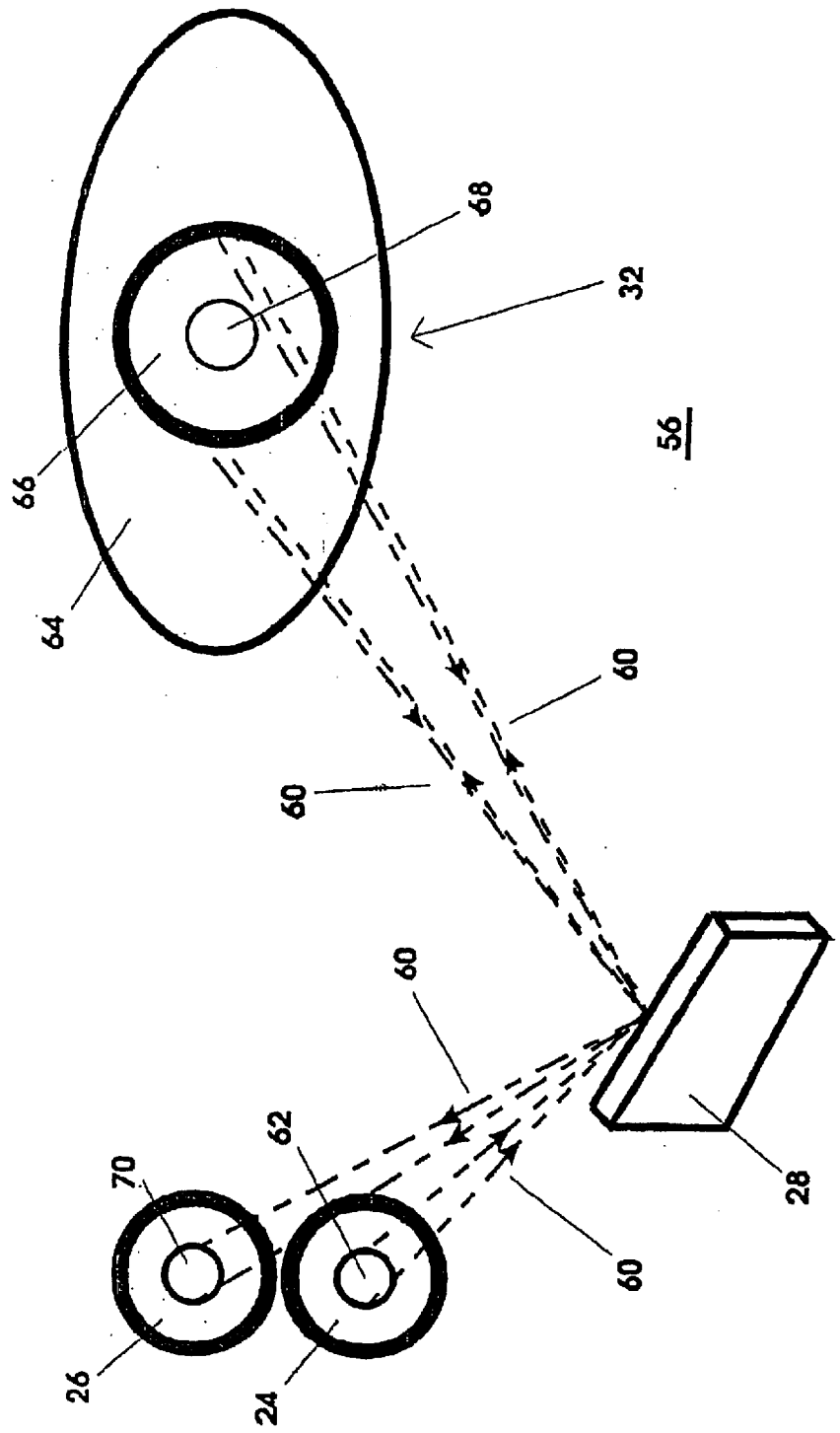
FIG. 5 depicts an embodiment for the physical eye-tracking system implemented with an infrared laser.

Shown in FIG. 5 is an example of an eye-tracking system 56. This system operates in a manner known to those of ordinary skill in the art. Several such systems are readily available, and the invention is not limited to any particular device, system, means, step or method for tracking the eye. For more detail on such eye-tracking systems, see for example the following U.S. Pat. Nos. 5,231,674; 5,270,748; 5,341,181; 5,430,505; 5,367,315; 5,345,281; 5,331,149 and 5,471,542 incorporated herein by reference. In its preferred form, a low power laser 24 generates an infrared eye-tracking laser beam 60. The laser beam is projected through a lens 62 and reflected by a mirror 28 onto the user's eye(s) 32. The user's eyes include a sclera 64, cornea 66, and pupil 68. When the user's eye(s) 32 move, the eye components cause distortions in the infrared laser beam, which are reflected back onto mirror 28, and then through a lens 70 into an infrared photodetector, infrared camera 26 or other type of photodetector. This distortion of the laser beam corresponds to the eye direction vector which can be measured accurately by eye-tracking electronics 73 (Shown in FIG. 4). Data defining the eye direction vector is subsequently transmitted from the eye-tracking electronics 73 to the command computer 36 through the communication links 52. For calibration, the eye-tracking optics which include mirror 28, lens 62, infrared camera 26, and laser 24, may be automatically adjusted for optimal performance through the use of computer controlled actuators (not shown).

It is expressly noted that, while separate eye-tracking electronics 73 are shown in the block diagram as carried by the heads-up display system 10, it is also possible to transmit the raw data from the infrared detector imaging device 26 to the command computer 36, which then determines the associated eye direction vectors. Likewise, the eye-tracking computer (and other electronics, if used) can be worn by the surgeon 12 on a belt or backpack (not shown).

Figure 6A:
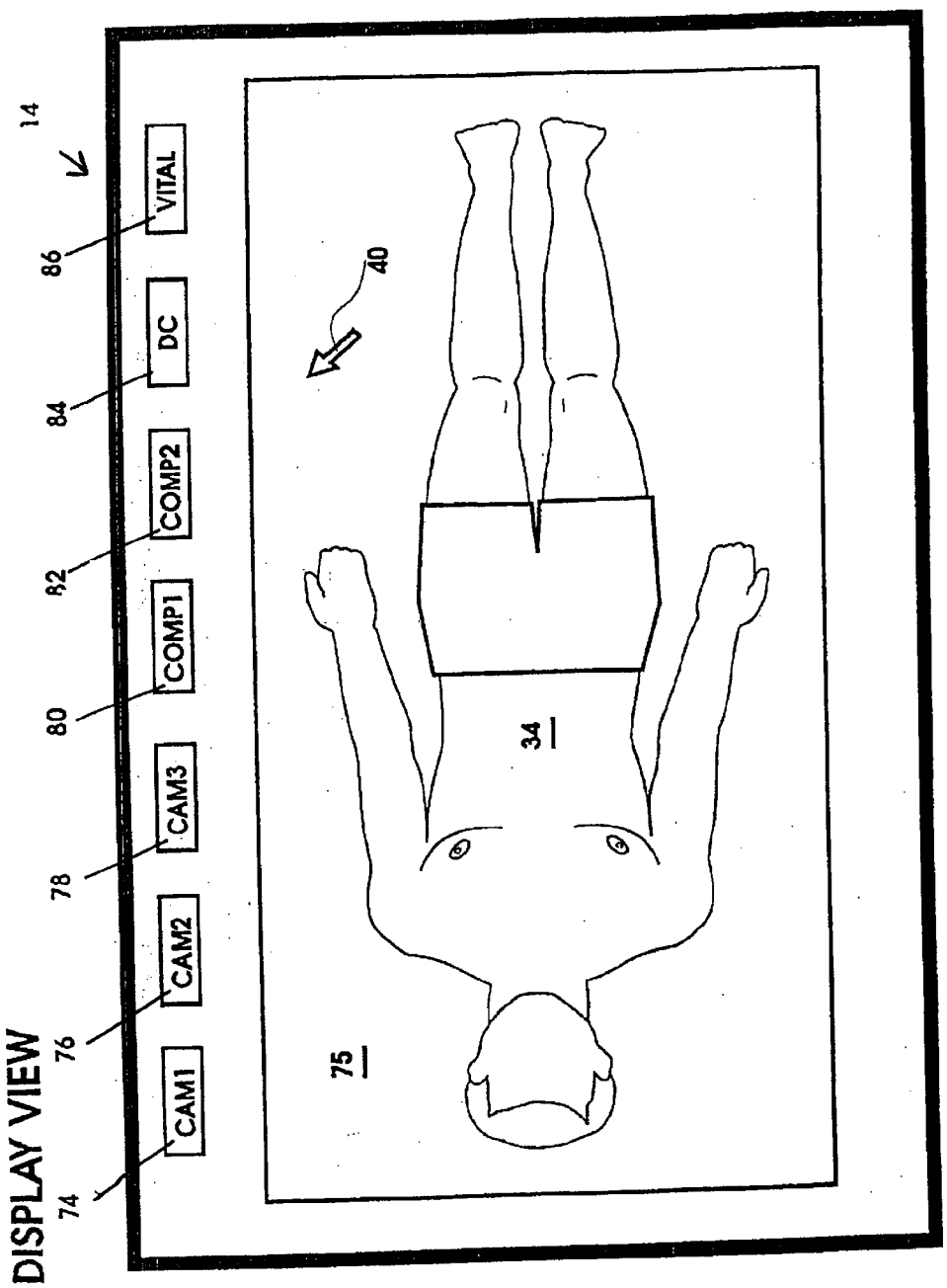
FIG. 6A depicts an embodiment for the display view and associated icons and menu items as seen by the surgeon wearing the heads-up display on a transparent or see-through screen.

Shown in FIGS. 6 and 7 are the contents and arrangement of several preferred forms of visual displays for the screen 14, including exemplary icons and menus for the user interface. Referring first to FIG. 6A, an object such a patient 34 is shown visible through the display 14 in the normal field of view 72 of the user 12. More specifically, a surgeon 12 wearing the HUD system 10 will see the patient 34 on table 75 through the semi-transparent display screen 14. The user will also see a number of icons or menu items 74, 76, 78, 80, 82, 84 and 86, superimposed over the real scene along the top portion of the normal field of view 72. Alternatively, the icons or menu items 74, 76, 78, 80, 82, 84, and 86 can be positioned along an opaque portion of the display screen 14, outside the normal field of view 72. The specific contents and form of the icon or menu items 74, 76, 78, 80, 82, 84, and 86, along with their associated computer operations, will vary depending on the specific implementation and programming. However, in its preferred form, there will be included icons or menu items that allow the user to control one or more cameras, access one or more computers, control the characteristics of the display 14, and display data, such as a patient's vital signs.

For example, as shown in FIG. 6A, three separate icons or menu items 74, 76 and 78, are assigned to control three cameras, indicated as CAM1, CAM2 and CAM3, respectively. By selecting any of these camera icons 74, 76, and 78, the user can independently control the associated camera systems to obtain (pan, tilt, rotate, zoom, etc.) and display various images. Similarly, two icons or menu items 80 and 82 are assigned to control access to two computers, indicated as COMP1 and COMP2, respectively. By selecting either of the computer icons, the user can access and control the associated computers or networks, to obtain patient data or other reference material. Another icon or menu item 84 is indicated with the label DC and is provided to allow the user to access and vary the characteristics of the screen 14. For example, the DC icon or menu item 84 can be accessed by the user to control brightness, contrast, and the degree to which you can see through the screen 14. Another icon 86 allows the user to control various devices to obtain and display on screen 14 any of a wide variety of vital signs.

Figure 6B:
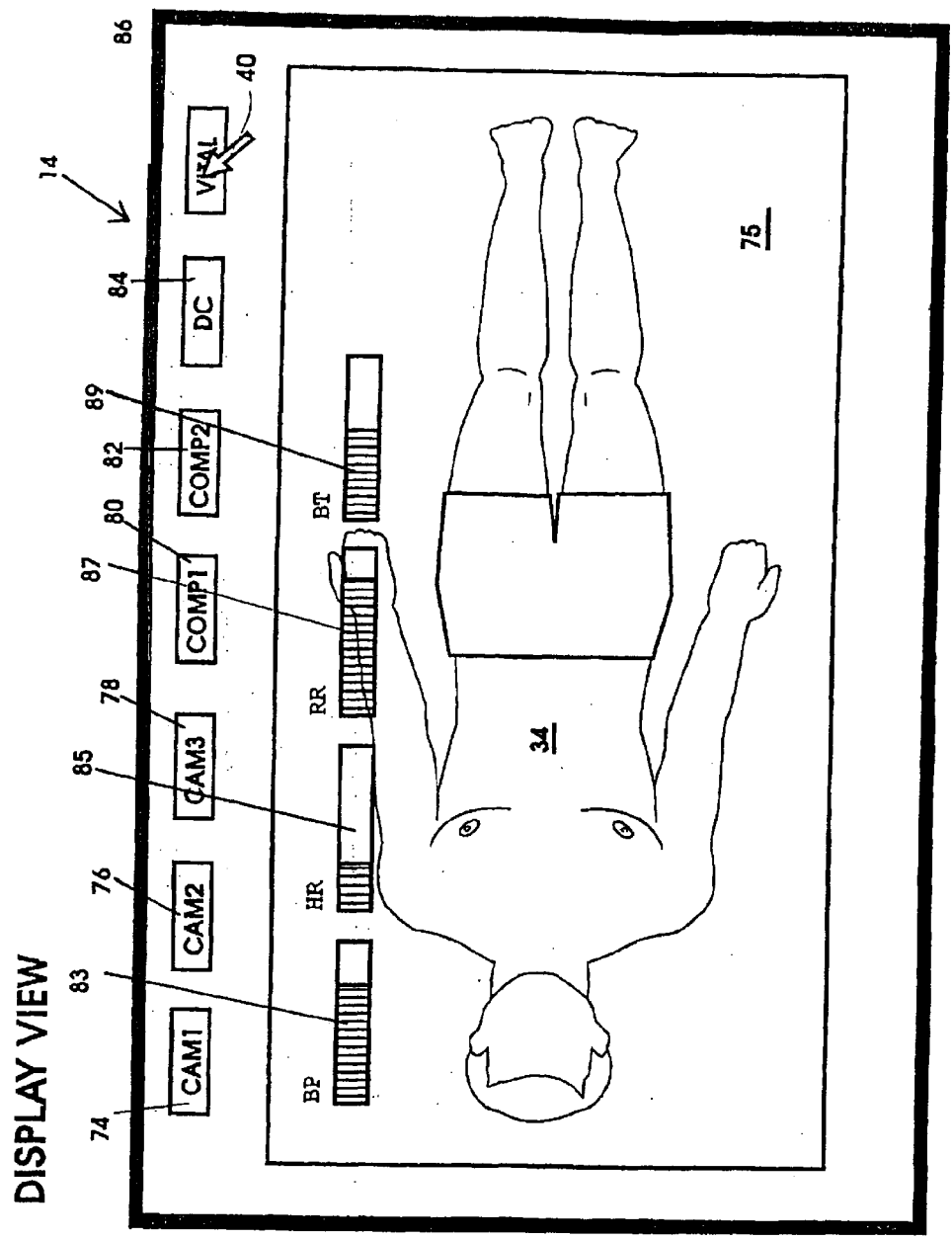
FIG. 6B depicts an embodiment for the display view and associated icons and menu items as seen by the surgeon wearing the heads-up display, with a patient's vital signs selected for display on a transparent or see-through screen.

As discussed above, each of the icons or menu items 74, 76, 78, 80, 82, 84, and 86 can be accessed and controlled by causing the eye-tracking cursor 40 to move over and select the desired icon. For example, referring to FIG. 6B, to see an update of the patient's vital signs, the surgeon can focus his or her eyes 32 on the icon 86 corresponding to the patient's vital signs. The eye-tracking system 56 will track the surgeon's eyes 32 to cause the cursor 40 to scroll to the VITAL icon 86. Depending on the programming of HUD system 10, when the cursor 40 tracks over the VITAL icon 86, the patient's vital signs will be superimposed over a portion of the surgeon's field of view 72. Shown in FIG. 6B is the display of the standard vital signs in analog graphic format. Specifically, graphics are shown for the patient's blood pressure 83, heart rate 85, respiratory rate 87 and body temperature 89. However, any additional vital sign (e.g., blood sugar, oxygen level, blood flow, etc.) can be programmed into the system and selected by the surgeon for display. In addition to, or in place of, the analog displays 83, 85, 87 and 89, digital values and titles can be displayed (not shown). Likewise, the system can be programmed to display the vital signs for a set period of time, continuously, or in an "on-off" fashion.

Figure 7A:
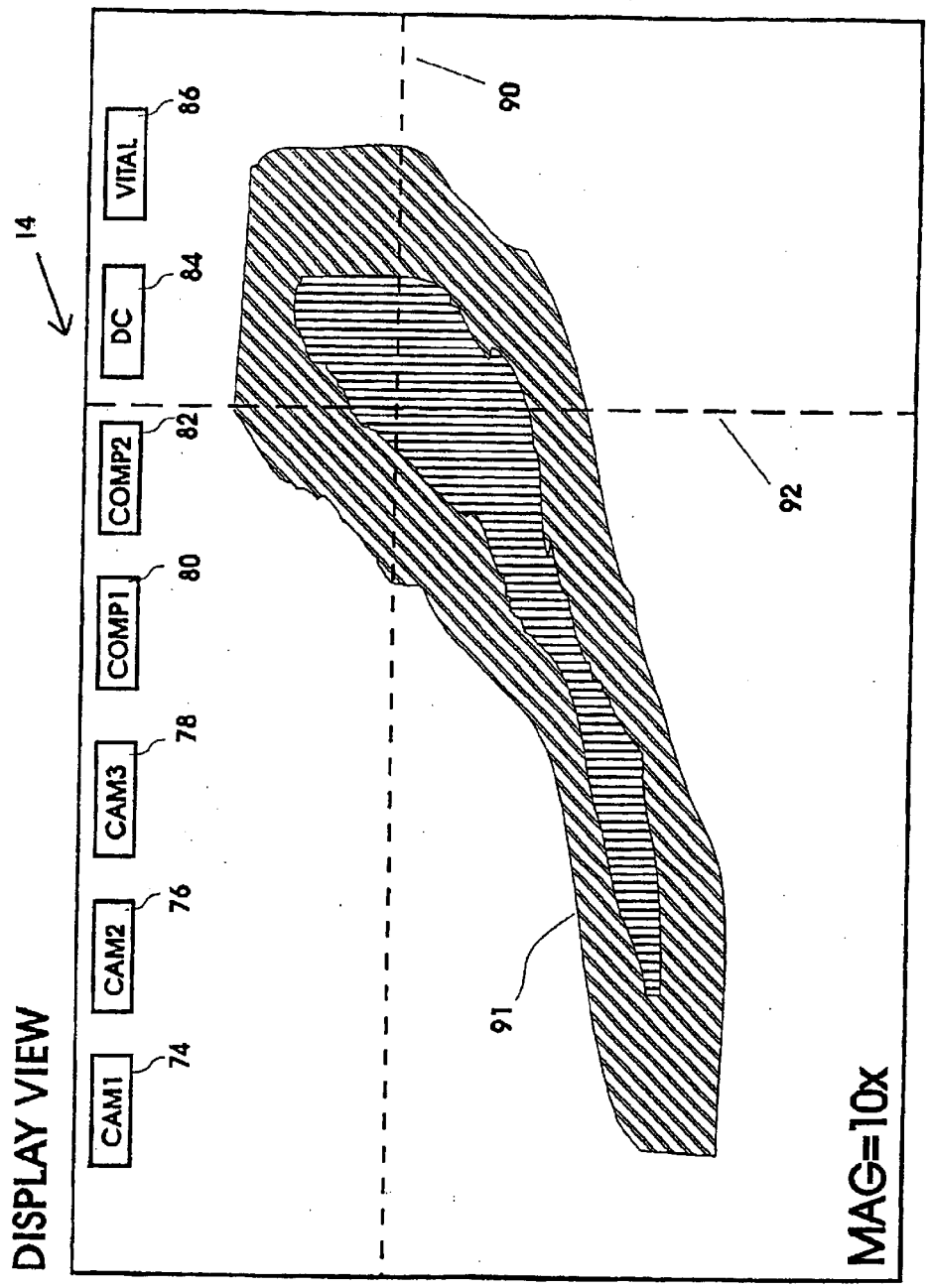
FIG. 7A depicts an embodiment for the display view and associated icons and menu items as seen by the surgeon wearing the heads-up display, with a view from one of the cameras selected for display on a portion of the screen that has been made selectively non-transparent.
Figure 7B:
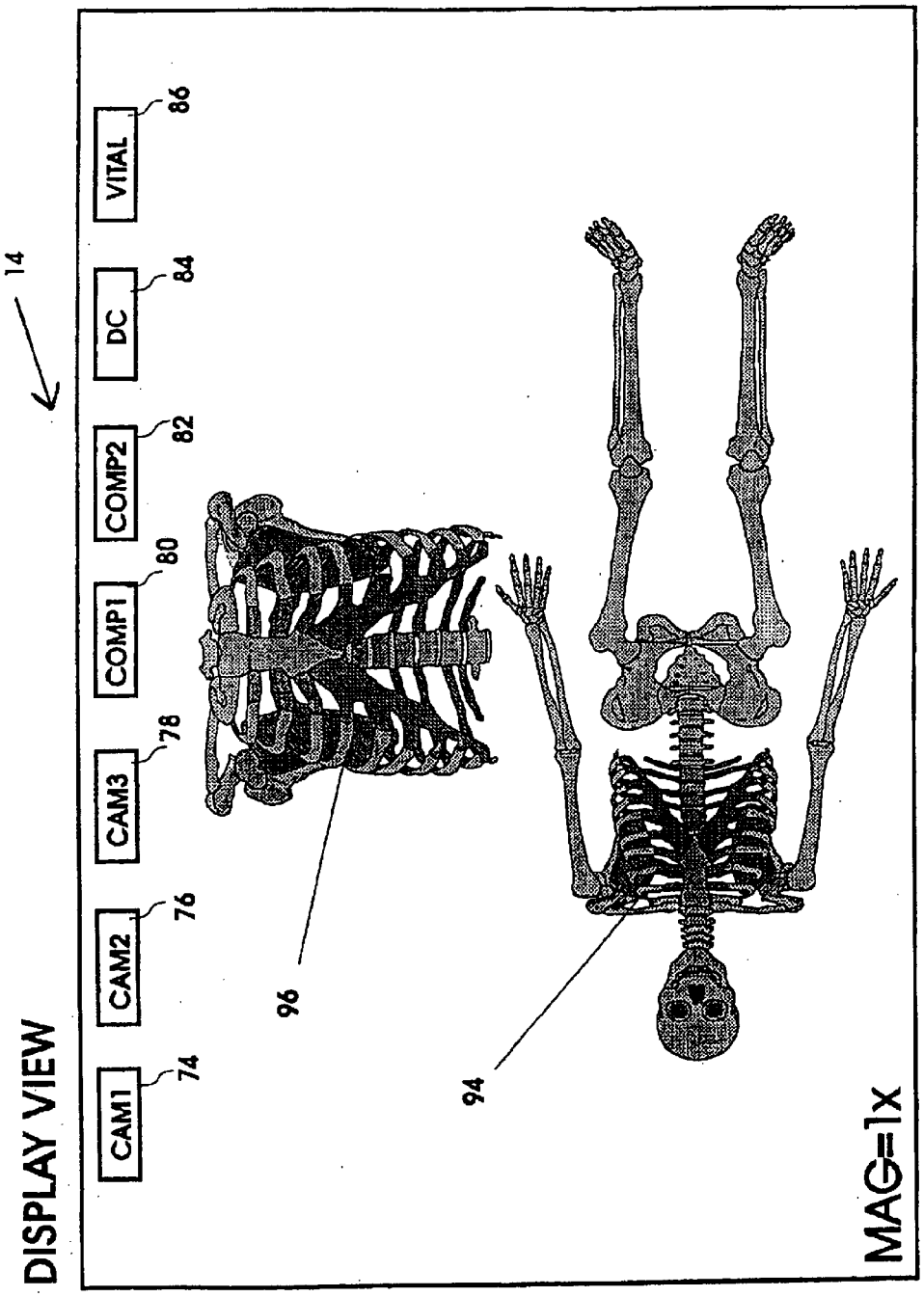
FIG. 7B depicts an embodiment for the display view and associated icons and menu items as seen by the surgeon wearing the heads-up display, with multiple x-ray images from the computer or one of the cameras selected for display on a portion of the screen that has been made selectively non-transparent.

Referring now to FIG. 6C, there is shown the same view as FIG. 6B, with an image captured by an image input device 38 superimposed on the normal field of view 72. To select a camera and display its image, the surgeon 12 focuses his eyes upon the associated icon, for example, the CAM1 icon 74. As above, the eye-tracking system 56 causes the cursor 40 to track to icon 74, and correspondingly initiates the desired camera image to be superimposed over the image of the patient 34. In the example shown in FIG. 6C, the image is a 5-times magnified image of an incision 91 in the patient. If desired, using appropriate menu icons, such as, for example, the display control icon 84, the surgeon may also cause the display screen 14 to operate in an opaque mode, displaying only the image of the incision 91 as if on a normal computer display screen. Likewise, the surgeon can magnify or otherwise control an image input device(s) 38 to obtain the image(s) desired, at the appropriate magnification. For example, FIG. 7A shows the display screen 14 operating in an opaque or semi-transparent mode with the incision 91 magnified to a 10-times view. Also shown in FIG. 7A, the cursor 40 has been replaced with a cross hair sighting system formed by dotted lines 90 and 92, thereby allowing the surgeon 12 to precisely select portions of the image to be still further magnified, enhanced, and/or centered in the display. By way of further example, reference is made to FIG. 7B, which depicts the display of skeletal FIGS. 94 and 96 selected as above by the surgeon 12 moving the cursor 40 to still another of the camera icons, for example, CAM2 icon 76.

If desired, the user interface and menu/icon programming can be configured to require the surgeon to take further action after the cursor 40 tracks over one of the icons. For example, and in the simplest form, once the surgeon causes the cursor to track over a selected icon, nothing may happen until the surgeon "clicks" a foot-operated mouse button (not shown). In more complex forms of the invention, the surgeon can actually access the selected operation by tracking the cursor to the selected icon and then speaking a select code word (e.g., "select" or "open") into microphone 16, which word or words are interpreted by speech recognition system 58. In still another form of the invention, the surgeon can access the selected operation associated with a particular icon or menu item by blinking a set number of times in quick succession after tracking the cursor 40 to the desired located. The blinking action is detected by the eye-tracking system 56.

In its simplest form, the selection by the surgeon of a specific icon will cause the associated data or images to be displayed on the screen 14. In such a mode of operation, it is desirable to include numerous icons on the periphery of the field of view 72, so that the surgeon 12 can quickly select an operation. In a more complex form of the invention, a series of menus can be associated with each icon, each menu having successively more detail. For example, instead of having three camera icons 74, 76 and 78, a single "video" icon can be substituted, which when selected by the cursor 40, will change the display to then show the individual icons for each of the many available cameras. Next, when one of the individual camera icons is selected by the cursor 40, the display will again change to show individual icons for the various camera controls, such to control the panning, tilting, rotating, magnification, filters, manipulator members, etc.

Figure 7C:
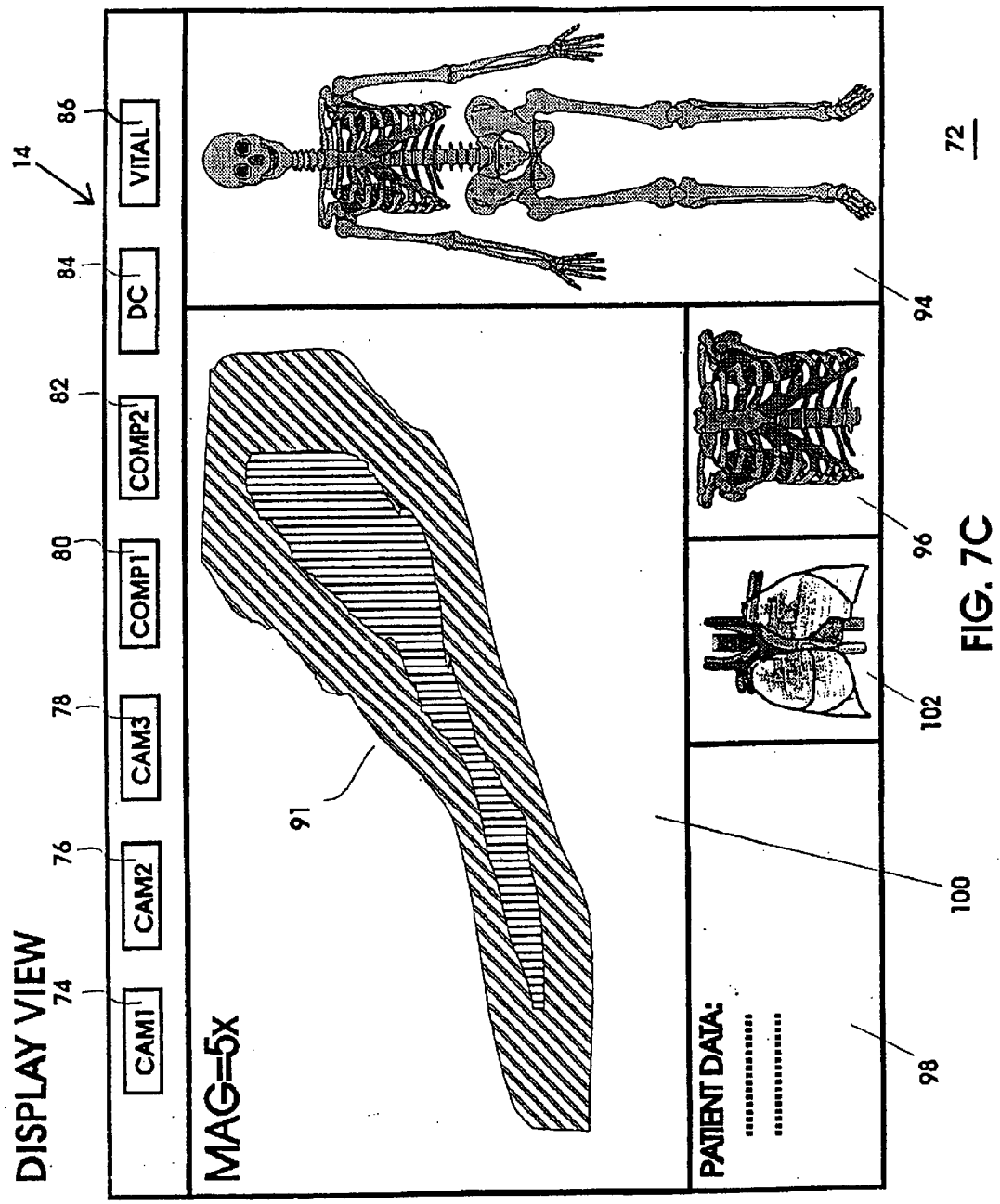
FIG. 7C depicts an embodiment for the display view and associated icons and menu items as seen by the surgeon wearing the heads-up display, with multiple forms of data and images displayed in windows on a portion of the screen.

As indicated, in more complex forms of the invention, the HUD system 10 may incorporate a hierarchical icon or menu system, where several layers of menus are necessary to obtain and display desired data. In that case, greater flexibility is desirable in controlling how much data can be displayed on the screen 14 at any given time. More specifically, as shown in FIG. 7C, in the more complex forms of the invention, the well known programming techniques from the Macintosh or Windows 95 operating systems are adapted and included in command computer 36 to allow the display of multiple windows, that can be easily tiled, cascaded, selected, re-sized, or hidden in a manner now familiar to those skilled in the art. Thus, once a specific camera is selected, the surgeon 12 can simply "hide" the image until it is again desired to view it, at which point it can be easily selected. Thus, the surgeon is not required to sequence through each of the menu levels to access the desired image. For example, as shown in FIG. 7C, the user has configured and controlled the display to show the windows or regions having patient data 98, magnified camera view 100, MRI data 102, magnified skeletal view 96, and whole body skeletal view 94. The surgeon 12 can independently hide, re-size, and rearrange each of the windows, along with the transparency level of the screen 14, thereby providing a maximum of flexibility.

The flexibility of the system is further shown in FIG. 7D, which depicts the display 14 having various user selected information, data, or images positioned thereon at varying degrees of intensity or transparency. For example, in FIG. 7D the surgeon has placed in the center of the display 14 a semi-transparent window 108 through which the normal field of view 72 displays the patient 34. When the surgeon's eyes 32 are focused on the window 108, the cursor 40 switches to the eye-tracking cross hairs 90 and 92. Under control of the eye-tracking system 56, the cross hairs 90 and 92 allow the surgeon 12 to select a specific portion of the patient 34, such as incision 91. The selected portion (e.g., part of the incision 91) of patient 34 is then locked on and magnified as a separate view in a different window 112 in the manner described above where a different set of selectable cross hairs 115 and 117 are shown for further magnification. As also shown in FIG. 7D, data such as the patient name and procedure description is displayed in the title portion 114 at the top of the display screen/surface 14. The surgeon 12 has selected more detailed patient data 116 to be displayed in a separate window 116 in the lower left hand corner of display 14. Various medication listings 118 and recommendations 120, along with current cursor or cross-hair coordinates 122 are displayed in a top portion of screen 14. Also selected for display are programmable warning indicators 124, 126, and 128, generally shown at the top right portion of the display screen/surface 14. The warning indicators may be programmed by the surgeon 12 to monitor certain conditions and to visually indicate warnings at desired levels. The same programmable warning indicators will issue various levels of audible warning tones to the surgeon 12 through the speaker 17. In the configuration of FIG. 7D, the surgeon 12, has selected and displayed the vital signs in a separate window 130 at the top left corner of the display screen/surface 14, and a 3D model of a select portion of the patient in window 132, which is continually updated, is shown below the vital signs 130 and updated in real time. Other graphical information 110 is updated in real time and displayed at the bottom right corner of the display screen/surface 14. Other pertinent images or data may be selectively displayed in other areas of the display 14, for example skeletal images in area 131 and magnetic resonant imaging (MRI) data 132. All of the described operations can also be effected or initiated by using the speech recognition system 58.

Thus, the overall medical HUD system 10 is extremely flexible, allowing each surgeon to customize the display and use only the features deemed appropriate, necessary and desirable. In the simplest operating mode, the surgeon may choose to display on a small part of the screen 14 only the patient's vital signs, as shown in FIG. 6B. In other modes, and depending on the procedure, the surgeon may elect to proceed in a semi-transparent mode, with several windows of data or images, as shown in FIG. 7D.

Each of the variations in programming set forth above can be configured for each specific surgeon 12 in a computer file assigned to that user and stored in command computer 36. Thus, if a particular surgeon 12 prefers to have specific icons or menus shown on specific screens, or for example, prefers digital over analog displays for vital signs, that user can select those specific settings and the system will perform in accordance therewith. Similarly, the system allows for substantial customization for specific types of surgeons or fields outside of surgery (e.g., microelectronics, forensics, etc.).

Figure 8C:
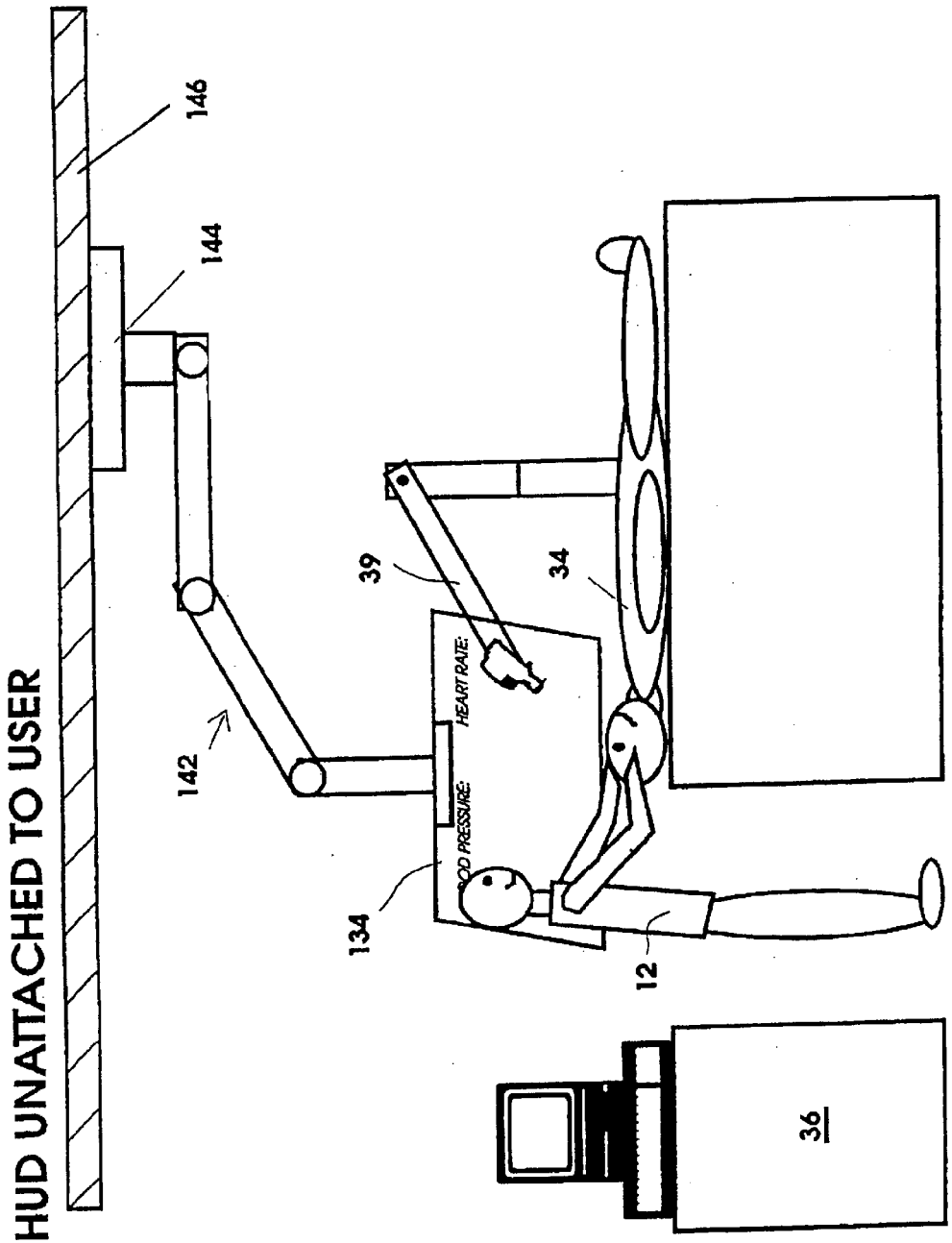

Shown in FIGS. 8A, 8B, and 8C is still another embodiment of the invention that incorporates a non-attached heads-up display screen 134. In FIGS. 8A and 8B, the display screen/surface 134 is shown as a generally flat rectangular semi-transparent display area. The display screen/surface 134 is attached to a top end of a sturdy but flexible post 136 via joint 138, thereby allowing it to be moved to various viewable positions. The joint 138 is also constructed to allow the screen 134 to be moved left or right relative to the post 136. The lower end of post 136 is attached to a base 140 that is supported on the floor. The post 136 is also adjustable in height and can be bent to allow precise positioning of the screen/surface 134 by the user. In a further modification to this non-attached HUD embodiment, as shown in FIG. 8C, the display screen 134 is mounted via robotic arm 142. Display screen/surface 134 of HUD 10 is attached at a lower end of the multi-jointed, robotic arm or other manipulator 142. The upper end of arm 142 is coupled to a mounting platform 144 that is fixed to the ceiling 146 of a room. Speech commands such as "Adjust Display On", "Adjust Display Off", "Up", "Down", "Left", "Right", "Forward", and "Backward" can be used for controlling the position of the retractable display screen/surface 134. Here the position of the display screen/surface 134 may be robotically controlled by speech signals from an operator 12. Such speech signals may be received by a microphone and processed by a speech recognition system which thereby sends signals to a robotic microcontroller that drives the appropriate actuators to position the display screen/surface 134 as desired.

In the embodiments of FIGS. 8A, 8B and 8C, the non-attached heads-up display system operates in a manner as described in the head-mounted HUD display embodiment of FIGS. 1–7, thereby allowing the surgeon to select and display data in a superimposed manner over the normal field of view of the patient 34. Both the speech recognition system 58 and eye-tracking system 56 can be used to move the cursor 40 to activate select icons or menus for operating computer 36 and display 134. However, in the modified forms of the invention shown in FIGS. 8A, 8B and 8C, additional methods for moving the cursor are possible, including using a low power laser mounted on head of the surgeon 12, along with a touch screen incorporated in display screen itself.

The foregoing description of a preferred embodiment and best mode of the invention known to applicant at the time of filing the application has been presented for the purposes of illustration and description. It is not intended to be exhaustive or to limit the invention to the precise form disclosed, and many modifications and variations are possible in the light of the above teaching. The embodiment was chosen and described in order to best explain the principles of the invention and its practical application, and to enable others skilled in the art to best utilize the invention in various embodiments and with various modifications as are suited to the particular use contemplated.

For example, many computer-controlled instruments used in the micro-electronics field have one or more eyepieces through which the operator views a specimen. The preferred embodiment of the heads-up display can be easily modified for use in such applications. More specifically, because the user's eye is relatively aligned with the eye-piece, the eye-tracking laser can be unobtrusively mounted in or below the eye-piece shaft. The user interface can be displayed by a display driver onto the same view seen through the eye-piece. In the same manner as described for the preferred embodiment, the user can see the full realm of data in the normal field of view, while simultaneously controlling the associated computer. Still further modifications are possible without departing from the spirit and scope of the invention.

The HUD system's ability to provide high resolution images directly in the field of view of an operator without forcing the operator to look away can greatly enhance the ability to complete an operation in a very precise and controlled manner. This precise control can be incorporated into surgical cutting, probing, and/or positioning tools by clearly presenting the position of such tools onto the display with respect to a patient and/or patient model obtained from real time imagery. This technique can be very advantageous in the event that the actual orientation or position of such tool(s) is unobtainable from an unassisted eye but requires direct visual control to operate.

What is claimed is:

1. A heads-up display system for use by a medical technician, the heads-up display system selectively controllable by the medical technician comprising:

a) a transparent heads-up display screen including a plurality of icons including a vital signs icon, the transparent heads-up display screen worn on the head of the medical technician, the transparent heads-up display screen positioned in the normal field of view of the medical technician;

b) a command control computer coupled to the transparent heads-up display screen and including an electronic storage device;

c) a communication network coupled to the command control computer and further comprising:
        i. a wide-area network for accessing medical data bases to be accessed by the medical technician and for communication and consulting with other medical technicians; and,
        ii. signal transmitters and receivers for communication of information and images derived from the procedure for remote viewing, thus establishing a remote telepresence for consultation, education or other medical purposes;

d) an eye-tracking system integrated with the transparent heads-up display system, the eye-tracking system supported on the head of the medical technician and coupled to the command control computer and configured,
        (i) to detect and track movement of one of the medical technician's eyes as the medical technician views the icons on the transparent heads-up display screen, and
        (ii) to communicate to the command control computer eye-tracking data corresponding to the movement of the medical technician's eye to the icons on the transparent heads-up display; and e) a user interface including:
        (i) an icon control program stored in the electronic storage device and configured to cause the command control computer to generate and maintain on the display screen a plurality of selectable control icons, including a vital sign icon in a manner that is superimposed over the normal field of view;

(ii) a cursor control program stored in the electronic storage device and configured to cause the command control computer to: (1) generate and maintain on the display screen a moveable cursor in a manner that is superimposed over the normal field of view; (2) translate the eye-tracking data communicated from the eye-tracking system into cursor control data; (3) apply the cursor control data to cause the cursor displayed on the display screen to move in a manner that tracks movement of the medical technician's eye; and (4) generate process control data when the cursor is tracked over and selects the vital sign icon; and (iii) a process control program stored in the electronic storage device and configured to cause the command computer to initiate specific control actions corresponding to the process control data generated when the eye-tracking cursor is moved to the vital sign icon.

2. The system of claim 1 wherein the heads-up display includes a display driver coupled to the command computer and configured so as to project images onto the display screen.

3. The system of claim 2 wherein the command computer is coupled to the heads-up display by a radio communication link.

4. The system of claim 3 wherein the command computer is coupled to the heads-up display by a wire communication link.

5. The system of claim 2 comprising a voice recognition system including:

a) a microphone placed proximate the user's mouth;

b) a speaker placed proximate at least one ear of the user;

c) a voice recognition circuit configured to recognize words spoken by the user and generate speech command signals corresponding thereto; and d) wherein the process control program is configured to cause the command computer to initiate specific control actions corresponding to the speech command signals generated by the voice recognition circuit.

6. The system of claim 1 wherein the icon control program generates and maintains on the display screen the vital sign icon relating to data acquisition procedures.

7. A hands-free system for assisting medical practitioners in the performance of medical procedures on patients comprising:

a. a computer subsystem coupled to a patient medical data base subsystem, a communication network subsystem, a patient monitoring sensor subsystem, and a heads-up display (HUD) subsystem worn on the head of the medical practitioner;

b. the computer subsystem further comprising:

i. one or more computers programmed to respond to patient sensor inputs and to external HUD commands from medical practitioners; to retrieve and record medical data base information; to manage information flow to and from the external communication network; to transmit medical images and information to the HUD; and, to perform analysis of information and present results of the analysis;

ii. signal processing circuitry coupled to the computer subsystem for processing command signals and sensor information signals for input to the computer, and to process signals from the computer for audio, visual or other presentation to the medical practitioners;

iii. a first communication link for communicating with the heads-up display subsystem;

c. the heads-up display (HUD) subsystem further comprising:

i. a second communication link for communicating with the computer subsystem first communication link and with: (1) a HUD camera and light subsystem, (2) a HUD eye-tracking subsystem, (3) a HUD display subsystem, (4) a HUD audio input subsystem; and, (5) a HUD speaker subsystem;

ii. the HUD camera and light subsystem coupled to the second communication link;

iii. the HUD eye-tracking subsystem coupled to the second communication link;

iv. the HUD display subsystem coupled to the second communication link;

v. the HUD audio input subsystem coupled to the second communication link;

vi. the HUD speaker subsystem coupled to the second communication link;

d. the medical data base subsystem coupled to the computer subsystem and further comprising:

i. patient data base information including medical history, medical images, allergic reactions, family history and related data;

ii. treatment information for various maladies and recommended procedures;

iii. medication alternatives; and, iv. surgical recommendations for different patient conditions;

e. the communication network subsystem coupled to the computer subsystem and further comprising:

i. a wide-area network for accessing medical data bases to be queried by the medical practitioner and for communication and consulting with other medical practitioners; and, ii. signal transmitters and receivers for communication of information and images derived from the procedure for remote viewing, thus establishing a remote telepresence for consultation, education or other medical purposes;

f. the patient monitoring sensor subsystem coupled to the computer subsystem and further comprising:

i. vital sign sensors comprising blood pressure, heart rate, respiration rate, body temperature, or other patient status indicators;

ii. signal generators coupled to the vital sign sensors for generating coded signals representative of the measured vital signs; and iii. communication circuitry coupled to the signal generators and the computer subsystem for formatting and transmitting sensor information to the computer sub-system;

g. the computer subsystem being further programmed to operate the HUD to provide a user selectable display options comprising:

i. patient images derived from the camera and lighting subsystem or from the computer data base information, including composite and overlay images, ii. sensor icons displaying sensor measurements from the patient monitoring sensor subsystems;

iii. control icons or menus to control various subsystems including the camera and lighting subsystem panning, tilting, magnification or zooming and lighting; the display subsystem; and one or more computer subsystems;

iv. hierarchical icon or menu operation with layers of menus;

v. multiple simultaneously viewable display windows arranged in tiled format with selected images, patient information, text information, or other related information, the display windows being semitransparent or opaque under user or under program control, individual windows being further selectable for expanded viewing, resizing, hiding, or rearrangement, vi. selectable, programmable warning indicators to visually indicate warnings at desired levels, vii. the display options being user selectable and controllable using the HUD eye-tracking subsystem by tracking the medical practitioner's eyes causing an eye tracking cursor to move over the display with user selection of the desired icon or menu by specific eye movements, a spoken command, or foot actuation of a system control to direct desired operations and displays.

8. The invention in accordance with claim 7 wherein the first communication link of the computer subsystem further comprises:

a wireless radio for transmission and reception of signals;

an antenna coupled to the wireless radio; and signal routing and control circuitry for routing various signals to and from the computer subsystem.

9. The invention in accordance with claim 8 wherein the second communication link of the HUD subsystem comprises:

wireless radio for transmission and reception of signals;

an antenna coupled to the wireless radio;

couplings to the HUD eye-tracking subsystem, display subsystem, audio input subsystem, camera and light subsystem and speaker subsystem for receipt and delivery of messages and signals to, from and between these HUD subsystems; and, signal routing and control circuitry for routing various signals to and from respective subsystems.

10. The invention in accordance with claim 9 wherein the HUD camera and light subsystem coupled to the second communication link comprises:

at least one imaging device, such as a CCD camera, an x-ray scanner, a NMR scanner, a CAT scanner, a sonic scanner, or other medical imaging scanner, coupled to a pan driver, a tilt driver, a magnification or zoom driver and an illumination light for capturing images of selected areas of a subject patient for display, analysis or recording, the imaging device being further coupled to the second communication link for delivery of images of selected areas of the patient to the computer subsystem and to the HUD display subsystems;

the pan driver coupled to the second communication link to receive control signals and further coupled to the imaging device to enable controllable panning of the subject patient with the imaging device to view different areas of the patient;

the controllable tilt driver coupled to the second communication link to receive control signals and further coupled to the imaging device to enable varying the viewing angle of the selected patient area with the scanning device the or zoom or magnification driver coupled to the second communication link to receive control signals and further coupled to the imaging device to enable controllable magnification of selected areas of a subject patient; and, the light receiving control signals to provide controllable illumination to selected areas of a subject patient to enhance user or imaging device visibility.

11. The invention in accordance with claim 10 wherein the HD eye-tracking subsystem coupled to the second communication link comprises:

a low powered laser coupled to the eye-tracking electronics for generating an infrared eye-tracking laser beam;

eye-tracking optics coupled to the eye-tracking electronics including a lens for focusing the laser beam onto a mirror positioned to reflect the beam onto the user's eye(s), and a mirror to positioned to capture reflected energy from the user's eye(s) and direct the reflected energy through a lens to an infra photo-detector camera;

eye-tracking electronics coupled to the infrared photo-detector camera for detecting distortion of the reflected laser beam energy corresponding to the eye direction vector, and generating data defining the eye direction vector for transmission through communication links to the computer subsystem; and, a calibration subsystem coupled to the eye-tracking subsystem elements for adjusting the elements for optimal performance through the use of computer controlled actuators.

12. The invention in accordance with claim 11 wherein the HUD display subsystem coupled to the second communication link comprises:

a display screen or transparent or semi-transparent surface mounted in the field of view of the medical practitioner using the HUD for the display of images;

display optics comprising mirrors or lenses for focusing of display images on the screen or surface for viewing by the medical practitioner, including capability for superimposing the display images over the real scene being viewed through the transparent or semitransparent HUD viewing surface; and, a display driver coupled to the second communication link for receiving display signal and generating the actual display image to be viewed by the medical practitioner.

13. The invention in accordance with claim 12 wherein the HUD audio input subsystem coupled to the second communication link comprises:

an audio input microphone mounted on the HUD to enable the user to use spoken commands to direct overall system operation or to record comments;

a speech recognition subsystem coupled to the audio microphone to recognize spoken commands and generate control signals; and, an input command interpreter subsystem coupled to the speech recognition subsystem and the second communication link to interpret commands from the speech recognition subsystem and generate computer commands for transmission to other system elements, including at least the computer subsystem.

14. The invention in accordance with claim 13 wherein the HUD speaker subsystem coupled to the second communication link comprises:

a speaker mounted on the HUD to enable the user to hear spoken or otherwise audible commands generated by the computer subsystem or relayed by that subsystem from the external communication subsystem or information database subsystem or from the patient; and, speaker control circuitry to adjust the speaker volume or other audio parameters for optimum performance in the working environment.

* * * * *